United States Patent
Sugiyama

(10) Patent No.: US 9,358,025 B2
(45) Date of Patent: Jun. 7, 2016

(54) MEDICAL DEVICE

(71) Applicant: Terumo Kabushiki Kaisha, Shibuya-ku, Tokyo (JP)

(72) Inventor: Hiromu Sugiyama, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 607 days.

(21) Appl. No.: 13/843,895

(22) Filed: Mar. 15, 2013

(65) Prior Publication Data

US 2013/0304117 A1 Nov. 14, 2013

Related U.S. Application Data

(63) Continuation of application No. PCT/JP2011/068064, filed on Aug. 8, 2011.

(30) Foreign Application Priority Data

Sep. 29, 2010 (JP) .................................. 2010-218517

(51) Int. Cl.
*A61B 17/28* (2006.01)
*A61N 7/02* (2006.01)
(Continued)

(52) U.S. Cl.
CPC ......... *A61B 17/2804* (2013.01); *A61B 17/0057* (2013.01); *A61B 18/1442* (2013.01); *A61B 18/1477* (2013.01); *A61B 18/1492* (2013.01); *A61N 7/022* (2013.01); *A61B 17/50* (2013.01); *A61B 18/1815* (2013.01); *A61B 18/20* (2013.01); *A61B 2017/0046* (2013.01); *A61B 2017/00243* (2013.01); *A61B 2017/00358* (2013.01); *A61B 2017/00513* (2013.01); *A61B 2017/00575* (2013.01); *A61B 2017/00606* (2013.01); *A61B 2017/00876* (2013.01); *A61B 2018/0038* (2013.01); *A61B 2018/0091* (2013.01);
(Continued)

(58) Field of Classification Search
CPC ............... A61B 17/0057; A61B 2017/00575; A61B 19/30; A61B 2019/304; A61B 2019/307; A61B 2017/00243; A61B 2018/0038; A61B 2017/00513; A61B 2018/0091; A61B 2017/0046; A61B 2017/00464; A61B 2017/00469; A61M 2025/09116; A61F 2002/4623; A61F 2002/4624
See application file for complete search history.

(56) References Cited

U.S. PATENT DOCUMENTS

2009/0018469 A1* 1/2009 Yanuma ................. A61B 10/04
600/569

FOREIGN PATENT DOCUMENTS

EP 2 184 019 A1 5/2010
EP 2 184 024 A1 5/2010
(Continued)

*Primary Examiner* — Katherine Rodjom
(74) *Attorney, Agent, or Firm* — Buchanan Ingersoll & Rooney PC

(57) ABSTRACT

A medical device is configured to prevent a member attached to the distal end of an operation wire passing through a catheter from dropping out from an operation wire. The medical device includes an operation wire which passes through a catheter and which is advanceable and retractable toward the axial direction with respect to the catheter, a distal member interlocked on the distal side of the operation wire, and a grasping unit which is interlocked on the proximal side of the operation wire. The medical device also includes a safety mechanism for releasing the interlock between the operation wire and the grasping unit by a load lower than the breaking strength between the operation wire and the distal member.

17 Claims, 18 Drawing Sheets

(51) Int. Cl.
*A61B 18/14* (2006.01)
*A61B 17/00* (2006.01)
*A61B 17/50* (2006.01)
*A61B 18/00* (2006.01)
*A61B 18/18* (2006.01)
*A61B 18/20* (2006.01)

(52) U.S. Cl.
CPC .............. *A61B2018/00589* (2013.01); *A61B 2018/00619* (2013.01)

(56) References Cited

FOREIGN PATENT DOCUMENTS

| | | |
|---|---|---|
| JP | 2006-521181 A | 9/2006 |
| WO | 93/21844 A1 | 11/1993 |
| WO | 2004/086944 A2 | 10/2004 |
| WO | 2007/100067 A1 | 9/2007 |
| WO | 2009/028285 A1 | 3/2009 |
| WO | 2009/028542 A1 | 3/2009 |

\* cited by examiner

MEDICAL DEVICE

CROSS REFERENCES TO RELATED APPLICATIONS

The present application is a continuation application of International Application No. PCT/JP2010/068064 filed on Aug. 8, 2011, and claims priority based on Japanese Patent Application No. 2010-218517 filed on Sep. 29, 2010, the entire content of both of which is incorporated herein by reference.

TECHNICAL FIELD

The present invention relates to a medical device and in particular, relates to a medical device which is inserted inside a body cavity.

BACKGROUND DISCUSSION

Recently, as a device for medically treating a patent foramen ovale (hereinafter, referred to as PFO) which is a cardiogenic factor in strokes and migraine headaches, there has been proposed a device described in International Application Publication No. WO/2007/100067. This publication describes a PFO closing device in which an apparatus is inserted into the foramen ovale from the right atrium toward the left atrium, a foramen ovale valve is pulled so as to close the foramen ovale by a pressing device which is bent inside the left atrium, the foramen ovale valve and the atrial septum secundum are sandwiched by a pair of electrodes, and the biological tissue is fused by applying electric energy from both the electrodes.

The pressing device is constructed so that by carrying out traction of an operation wire extending from the operation unit on the hand side of the device to the distal portion thereof toward the pull-out direction at the hand side operation unit, a distal member fixed at the distal end of the operation wire is moved to the hand side (proximally) and by utilizing the moving force of this distal member, the operation wire bends the passing-through member at the distal portion of the device.

When a foreign object gets mixed inside a blood vessel, there is a fear that the foreign object is carried to the brain by the blood flow and a cerebral infarction is caused. Therefore, when pulling the operation wire in order to bend the pressing device, it is necessary to adjust the traction force such that the distal member fixed on the operation wire does not drop out by any possibility.

SUMMARY

The medical device disclosed here exhibits high safety in which a member to be attached to the distal end of the operation wire which is inserted-through a catheter is inhibited or prevented from dropping out from the operation wire.

The medical device according to one aspect of the disclosure here includes a catheter, an operation wire passing through the catheter and being advanceable and retractable in an axial direction with respect to the catheter, a distal member interlocked on the distal end of the operation wire, a grasping unit interlocked on the proximal end of the operation wire, and a safety mechanism for releasing the interlock between the operation wire and the grasping unit by a load lower than a breaking strength between the operation wire and the distal member.

The safety mechanism releases the interlock between the operation wire and the grasping unit by a load lower than the breaking strength between the operation wire and the distal member, so that even if an excessively strong traction force is applied to the operation wire, the proximal member is released from the operation wire before the distal member breaks from the operation wire. Consequently, the possibility that the distal member drops out from the operation wire is prevented, and safety is improved by the fact that the distal member is not left-behind inside the living body and by preventing the possibility of causing a cerebral infarction which is caused by a phenomenon in which the distal member is carried to the brain by the blood flow.

The safety mechanism can be made to include a proximal member which is fixed on the proximal side of the operation wire and concurrently, which is interlocked with the grasping unit and breaks with respect to the operation wire by a load lower than the breaking strength between the operation wire and the distal member. The proximal member thus breaks with respect to the operation wire before the distal member breaks from the operation wire even if applying a strong traction force to the operation wire, and so the possibility that the distal member may drop out from the operation wire is prevented, and safety is improved.

The proximal member is preferably larger than the outer diameter of the operation wire, and the grasping unit includes a proximal end restriction-hole having a size through which the operation wire passes and concurrently, through which the proximal member cannot pass. The cross-sectional area of the interlock portion with respect to the proximal member of the operation wire is smaller than the cross-sectional area of the interlock portion with respect to the distal member of the operation wire, and so it is possible to break the interlock portion with respect to the proximal member of the operation wire before the distal member breaks from the operation wire.

The breaking strength of the proximal member is lower than the breaking strength between the operation wire and the distal member, and so it is possible to break the proximal member before the distal member breaks from the operation wire.

The safety mechanism is provided at the grasping unit and includes a wire-hold portion for holding the operation wire by a holding power in which the operation wire is disengaged by a load lower than the breaking strength between the operation wire and the distal member. It is thus possible to make the operation wire disengage from the wire-hold portion before the distal member breaks from the operation wire.

A large diameter portion larger than the outer diameter of the operation wire can be fixed to the operation wire, and at the proximal end of the catheter, there can be formed a movement restriction-hole having a size through which the operation wire passes and concurrently, through which the large diameter portion cannot pass toward the proximal end direction. The pulling movement of the operation wire thus becomes impossible when the large diameter portion reaches the movement restriction-hole by the traction of the operation wire, and the uprise of the tensile force between the operation wire and the distal member is restricted, and so the possibility that the distal member drops out from the operation wire is prevented.

According to another aspect, a medical device comprises: at least one tubular member having a through hole, the at least one tubular member including a catheter sized and configured to be positioned in a living body, and the through hole at the distal end of the tubular member possessing a size; an operation wire positioned in the through hole and passing through the at least one tubular member so that a proximal end of the operation wire extends proximally beyond a proximal end of the at least one tubular member and a distal end of the operation wire extends distally beyond the distal end of the at least one tubular member, with the operation wire being axially movable in distal and proximal directions relative to the at least one tubular member; and a distal member connected to the distal end of the operation wire at a connection, with the distal member being positioned distally of the distal end of the at least one tubular member, and the distal member being disconnectable from the operation wire when a load is applied to the connection which exceeds a breaking strength of the connection. The distal member possesses a size greater than size of the through hole at the distal end of the tubular member so that the distal member is prevented from entering the through hole in the at least one tubular member when the operation member is axially moving in the proximal direction. A grasping unit is connected to the proximal end of the operation wire at a connection, and a safety mechanism is operatively associated with the grasping unit and the proximal end of the operation wire which causes the grasping unit to be disconnected from the operation wire when a load less than the breaking strength is applied to the connection of the grasping unit to the operation wire.

BRIEF DESCRIPTION OF DRAWINGS

FIGS. 11A and 11B are plan views showing the hand-side operation unit when a needle operation lever is operated, in which FIG. 11A shows a state before the operation and FIG. 11B shows a state after the operation.

FIGS. 12A and 12B are enlarged plan views showing the hand-side operation unit when a slide portion is moved backward, in which FIG. 12A shows a state in the midst of the backward moving and FIG. 12B shows a state after the backward moving.

FIGS. 19A and 19B are cross-sectional views showing a grasping unit of the PFO closing device according to a second embodiment disclosed by way of example, in which FIG. 19A shows a state before the breaking of the proximal member and FIG. 19B shows a state after the breaking of the proximal member.

FIGS. 20A and 20B are cross-sectional views showing a grasping unit of the PFO closing device according to a third embodiment disclosed as another example, in which FIG. 20A shows a state before the breaking of the proximal member and FIG. 20B shows a state after the breaking of the proximal member.

FIGS. 21A and 21B are cross-sectional views showing a grasping unit of the PFO closing device according to a further example, in which FIG. 21A shows a state before the breaking of the proximal member and FIG. 21B shows a state after the breaking of the proximal member.

FIGS. 23A and 23B are cross-sectional views showing a grasping unit of the PFO closing device according to another embodiment disclosed by way of example, in which FIG. 23A shows a state before the proximal member disengages from the grasping unit and FIG. 23B shows a state of the proximal member after the disengagement.

DETAILED DESCRIPTION

Figure 1:
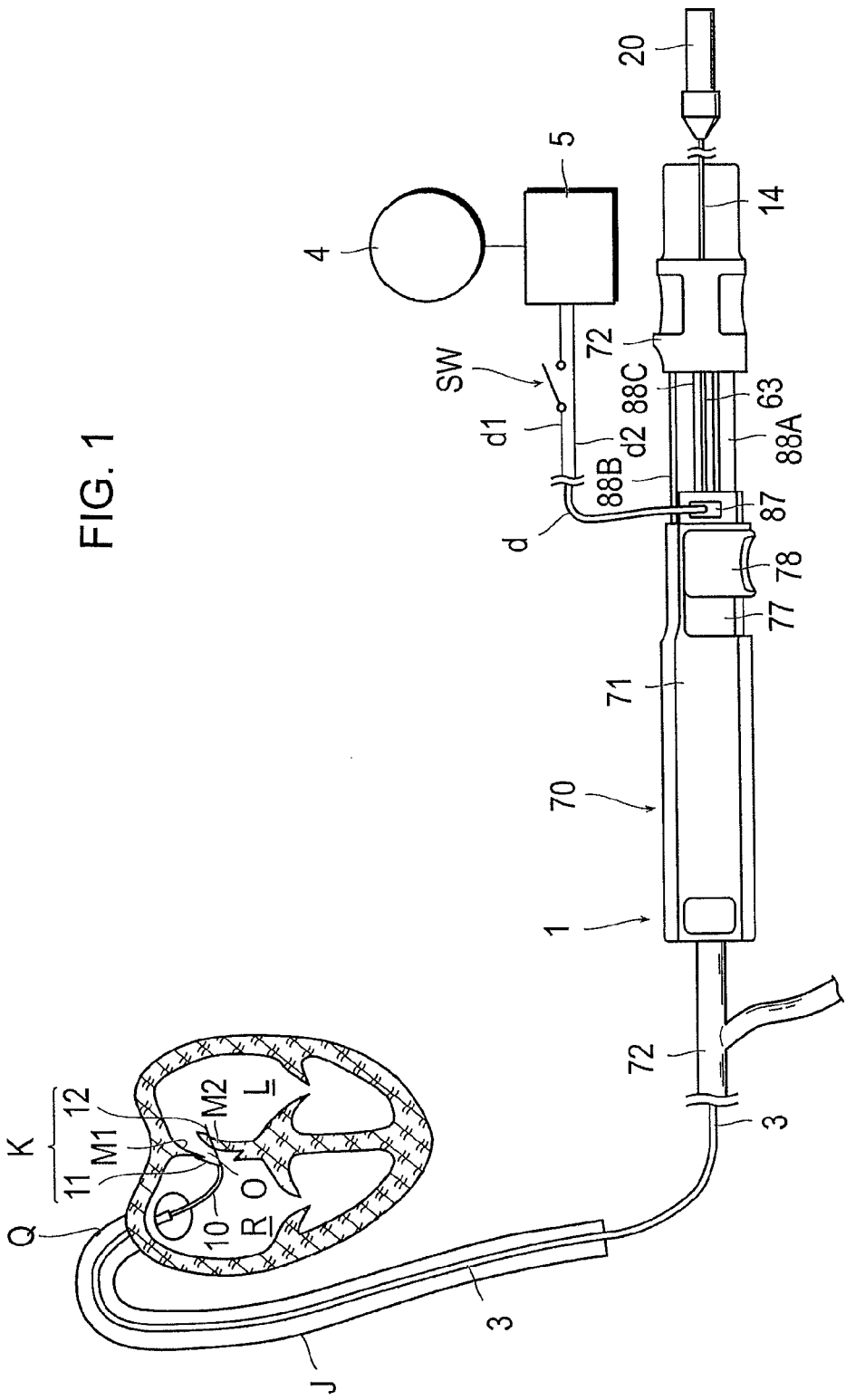
FIG. 1 is a schematic cross-sectional view showing a PFO closing device relating to a first embodiment disclosed by way of example.

Set forth below with reference to the accompanying drawing figures is a detailed description of embodiments of the medical device disclosed here. These disclosed embodiments represent examples of the inventive medical device disclosed here. To assist the clarity of the drawing illustrations and facilitate an understanding of features of the medical device and, the size ratio in the drawing figures may be exaggerated and different from the actual ratio.

Figure 2:
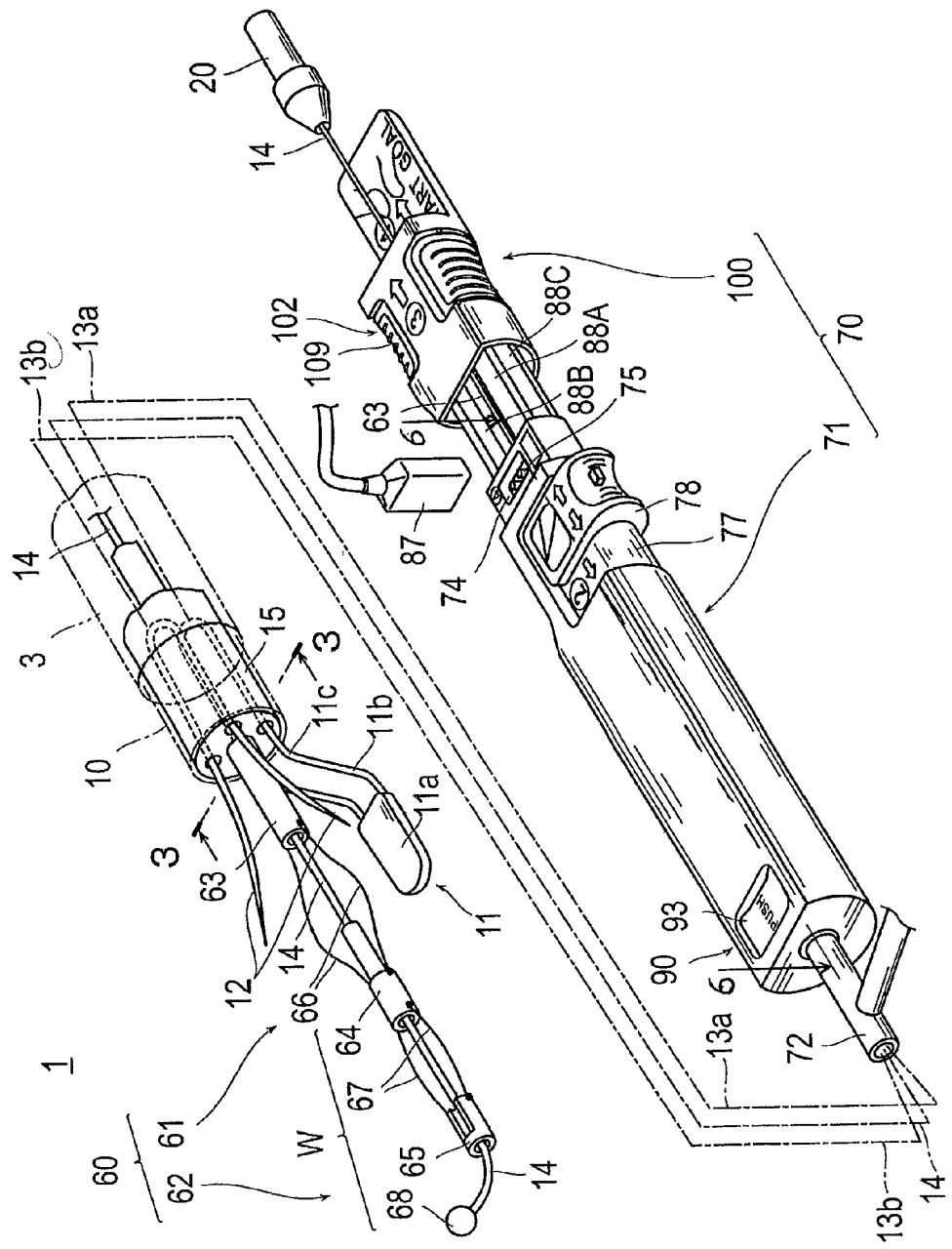
FIG. 2 is a perspective view of a portion of the PFO closing device shown in FIG. 1.
Figure 3:
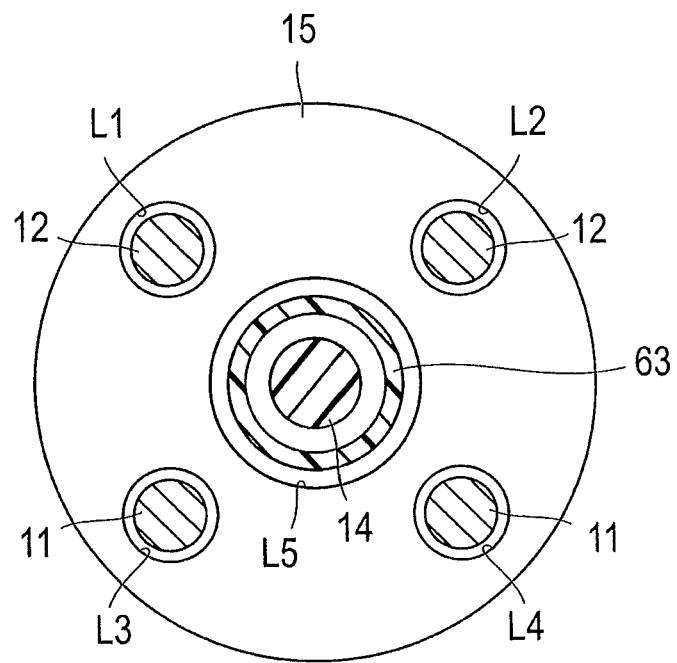
FIG. 3 is a cross-sectional view of a catheter distal portion taken along the section line 3-3 in FIG. 2.

A medical device according to a first embodiment is a PFO closing device, and a general overview of features of the PFO closing device will be explained first with reference to FIGS. 1-3. In FIG. 2, due to limitations of space, there is a description in a state in which only a hand-side operation unit 70 is demagnified.

The PFO closing device includes a catheter 1 constituted by a hand side operation unit 70 (proximal side operation unit) at the proximal end of a catheter main body 10, a guiding catheter 3 whose proximal end is interlockable with the hand side operation unit 70 and into the inside of which is insertable the catheter main body 10, and an energy supply means 4 supplying electric energy for fusing or necrotizing (when electrical energy is supplied to the electrodes, biological tissue sandwiched between the electrodes is fused and thermal denaturation or tissue hardening by ablation can occur in biological tissue around the electrodes) biological tissue M (generic term of M1, M2). The catheter 1 is provided at the distal portion of the catheter main body 10 and includes clamping means K for sandwiching a foramen ovale valve M2 and an atrial septum secundum M1, and a positioning hold means 60 for stably and accurately carrying out the clamping procedure by the clamping means K (see FIG. 2). In the following explanation, the hand side operation unit 70 side is referred to as the "proximal side" and the clamping means K side is referred to as the "distal side". Also, the term "catheter" refers to a tubular body used for medical use.

On an occasion of using the device, first, the guiding catheter 3 is inserted, for example, from a femoral vein J, and this guiding catheter 3 is inserted in a state in which, in the inside of the catheter, the clamping means K provided at the distal end of the catheter body 10 is stored together with the catheter body 10. After the distal end of the guiding catheter 3 reaches the region of the heart at which the procedure is to be performed, the clamping means K is caused to protrude from the catheter body 10 by operating the hand-side operation unit 70, and the tissues of the atrial septum secundum M1 and the foramen ovale valve M2 of the heart in which there occurs a defect O of a foramen ovale (this is sometimes referred to simply as foramen ovale O) are sandwiched. In this sandwiched state, the clamping means K is supplied with electric energy, both the tissues are heated and fused, and the defect O is closed. The clamping means K thus operates as a heating unit. In FIG. 1, "L" denotes a left atrium and "R" denotes a right atrium.

The clamping means K includes a sandwich member 11 directly contacting one side surface of the atrial septum secundum M1 and a sticking member 12 which is stuck into (punctures) the foramen ovale valve M2. The sandwich member 11 includes, as shown in FIG. 2, a flat-plate (plate-shaped) portion 11a having an overall flat plate shape and a pair of wire portions 11b connected to the proximal portion of the plate-shaped portion 11a; and the flat surface position of the plate-shaped portion is restricted (controlled) by several lumens L3, L4 (see FIG. 3) provided in a distal end tip 15 fixed to (locate at) the distal end of the catheter body 10. Also, the sandwich member 11 is connected to an operating member 13a by virtue of the operating member 13a being connected to the proximal end portion of the wire member 11b. In the illustrated embodiment, the wire members 11b are two legs of a U-shaped member. By advancing and retracting the operating member 13a in the axial direction, the sandwich member 11 protrudes from the distal end tip 15 and forms a predetermined sandwich width with respect to the sticking member 12 so as to sandwich the biological tissue M by approaching the sticking member 12 side when the wire members 11b enter into the distal end tip 15.

The sticking member 12 is held by lumens L1, L2 (see FIG. 3) formed in the distal end tip 15 so as to be movable forward and backward in a state in which the flat surface position of the sticking member 12 is restricted (the sticking members 12 tend to remain in a common plane as the sticking member 12 moves forward and backward). The sticking member 12 is movable so that the distal portion of the sticking member 12 is retractable into the distal end tip 15 by operating an operating member 13b connected to the proximal end of the sticking member 12. In the illustrated embodiment, the sticking member 12 is configured as two spaced apart needle members connected to one another and together forming a U-shaped member whose proximal end is connected to the operating member 13b. In the illustrated embodiment, the distal end portions of the needle members diverge away from one another in the distal direction as shown in FIG. 2.

The sticking member 12 exhibits elasticity such that very fine two needle members whose cross-sections perpendicular to the axes are circles and whose distal ends are sharply pointed are mutually separated, and also, the distal end thereof is relatively widely opened when the sticking member 12 protrudes in the forward or distal direction beyond the distal-mots end of the sticking member 12. It is possible for the number of needle members either to be one piece or to be three pieces or more.

The sandwich member 11 and the sticking member 12 both operate as electrode members (heating units), and the operating members 13a, 13b which push-out the sandwich member 11 and the sticking member 12 retractively from the catheter body 10 (see FIG. 2) are connected electrically with the energy supply means 4 through an input connector 75 which is positioned inside the catheter body 10 and which is provided at the hand-side operation unit 70 mentioned later, an output connector 87 which is a plug fitted with the input connector 75 (see FIG. 1), and a conduction wire d (collective designation of d1, d2) connected with the electrode terminal of the output connector 87 and a control unit 5. Either one of the conductive wires d1 and d2 (conductive wire d1 in this embodiment disclosed by way of example) is provided with a foot switch SW to be installed at the operator's feet in order to ON/OFF control the electric current from the energy supply means 4. Note that it is allowed, the foot switch SW, to employ a switch which can easily be operated on the hand-side.

The hand-side operation unit 70 is a unit for operating the clamping means K composed of a pair of electrode members which sandwich the biological tissue M lying in the vicinity of a defect existing in the biological tissue such that the clamping means K is pushed out freely from the distal end of the catheter body 10. The hand-side operation unit 70 is configured, as described below, such that it is possible to carry out all operations within that small area without moving a hand so much.

The hand-side operation unit 70 is provided, as shown in FIG. 2, with a needle operation lever 78 for operating the sticking member 12 which is one electrode member, a slide portion 100 for operating the sandwich member 11 which is the other electrode member, an operation wire 14 which is a rod for assisting the operating of the clamping means K and which passes through movably in the axial direction inside the hand-side operation unit 70 and the catheter body 10, a grasping unit 20 to be interlocked with the proximal portion of the operation wire 14 in order to operate the operation wire 14, a pusher piece 109 which operates a lock & unlock mechanism 102 for locking/unlocking the slide movement of the slide portion 100 (see FIG. 8) and concurrently, which locks the movement of the operation wire 14 in the axial direction, and an input connector 75 provided with an electrode terminal to be connected with energy supply means 4 for applying thermal energy.

Figure 4:
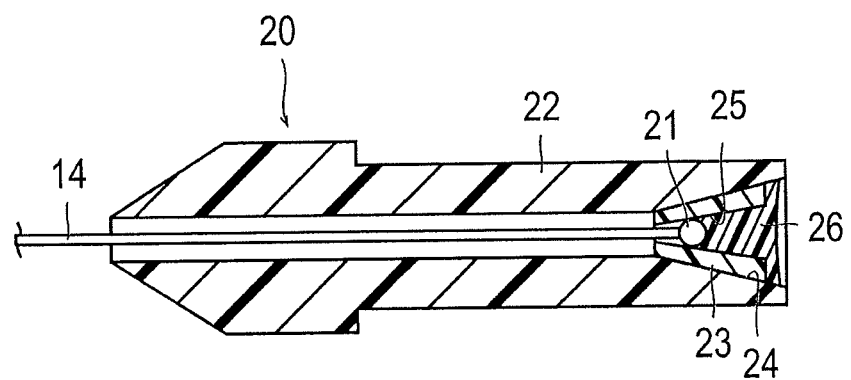
FIG. 4 is a cross-sectional view of a grasping unit of the PFO closing device.

A distal member 68 is provided as the distal end of the operation wire 14, and a proximal member 21 is provided at the proximal end of the operation wire 14 (see FIG. 4). The distal member 68 and the proximal member 21 have diameters larger than the outer diameter of the operation wire 14 and the cross-section area of the interlock portion between the operation wire 14 and the proximal member 21 is configured to be smaller than the cross-sectional area of the interlock portion between the operation wire 14 and the distal member 68. For the material of the operation wire 14, it is possible to apply, for example, a nickel-titanium alloy, a stainless steel and the like, but the material forming the operation wire 14 is not limited to these listed materials. Also, for the materials of the distal member 68 and the proximal member 21, it is possible to use, for example, a nickel-titanium alloy, a silver solder and the like, though once again the materials forming the distal member 68 and the proximal member 21 are not limited to these listed materials. The distal member 68 and the proximal member 21 are fixed with respect to the operation wire 14 by known technology such as welding, bonding, fusion or the like corresponding to the material, or it is possible for the distal member 68 and the proximal member 21 to be formed after being deformed by fusing the end portions of the operation wire 14 which is composed of a metal or a resin. The distal member 68 and the proximal member 21 have spherical shapes in this embodiment which serves as one example, but they are not necessarily limited to spherical shapes.

A manner of making the cross-sectional area of the interlock portion with respect to the proximal member 21 of the operation wire 14 smaller than the cross-sectional area of the interlock portion with respect to the distal member 68, chemical polishing can be applied rather easily, but mechanical polishing can be employed or it is possible to use, from the beginning, as the material of the operation wire 14 a wire having different outer diameters at the distal portion and at the proximal portion. With an operation wire 14 having this construction, the breaking strength with respect to the tensile force between the operation wire 14 and the proximal member 21 is lower than the breaking strength with respect to the tensile force between the operation wire 14 and the distal member 68.

As shown in FIG. 4, the grasping unit 20 includes a tubular grasping unit main body 22 through which the operation wire 14 passes and a proximal end fixing member 23 which is fixed on the proximal side of the grasping unit main body 22 and with which the proximal member 21 is interlocked. A taper-shaped tapered opening portion 24 is formed on the proximal side of the grasping unit main body 22, and a tubular proximal end fixing member 23 is fitted into this tapered opening portion 24. The tubular proximal end fixing member 23 has a proximal end restriction-hole 25 which is a taper-shaped through-hole whose inner diameter is reduced toward the distal end direction. The operation wire 14 is inserted into or through this proximal end restriction-hole 25 from the distal side of the operation wire 14, and the proximal member 21 is held in contact with the inner wall surface of the proximal end restriction-hole 25. The proximal member 21, the proximal end fixing member 23 and the grasping unit main body 22 are bonded by an adhesive agent 26 which is injected from the proximal side of the tapered opening portion 24. When injecting the adhesive agent 26, because the proximal member 21 has a spherical shape and the proximal end restriction-hole 25 is a taper-shaped hole, the proximal member 21 closely contacts the proximal end restriction-hole 25 and the adhesive agent 26 does not enter into the region in which the operation wire 14 and the proximal member 21 are interlocked. For this reason, the operation wire 14 is interlocked with the grasping unit 20 only through the proximal member 21, and the breaking strength between the operation wire 14 and the proximal member 21 does not come under the influence of the adhesive agent 26.

Examples of the materials forming the grasping unit main body 22 and the proximal end fixing member 23 include polycarbonate (PC), a polyacetal resin (POM) and the like, though the material is not limited in this regard.

In the above description, the breaking strength is evaluated depending on the large or small value of the cross-sectional area of the operation wire 14, but when the proximal member 21 (or distal member 68) breaks, there may occur a shared destruction depending on the shape or the like of the proximal member 21 (or distal member 68) and in this case, it is also possible to make the evaluation according to the shear cross-sectional area.

Figure 5:
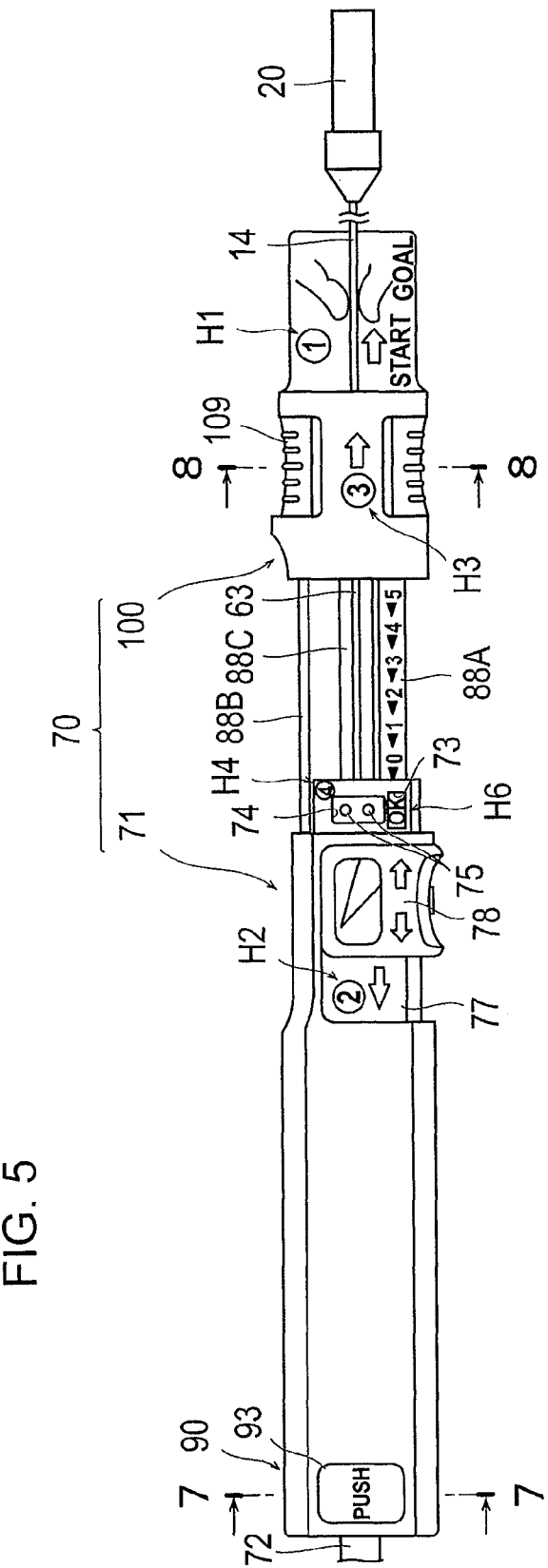
FIG. 5 is a plan view of the hand-side operation unit of the PFO closing device shown in FIG. 1.
Figure 11:
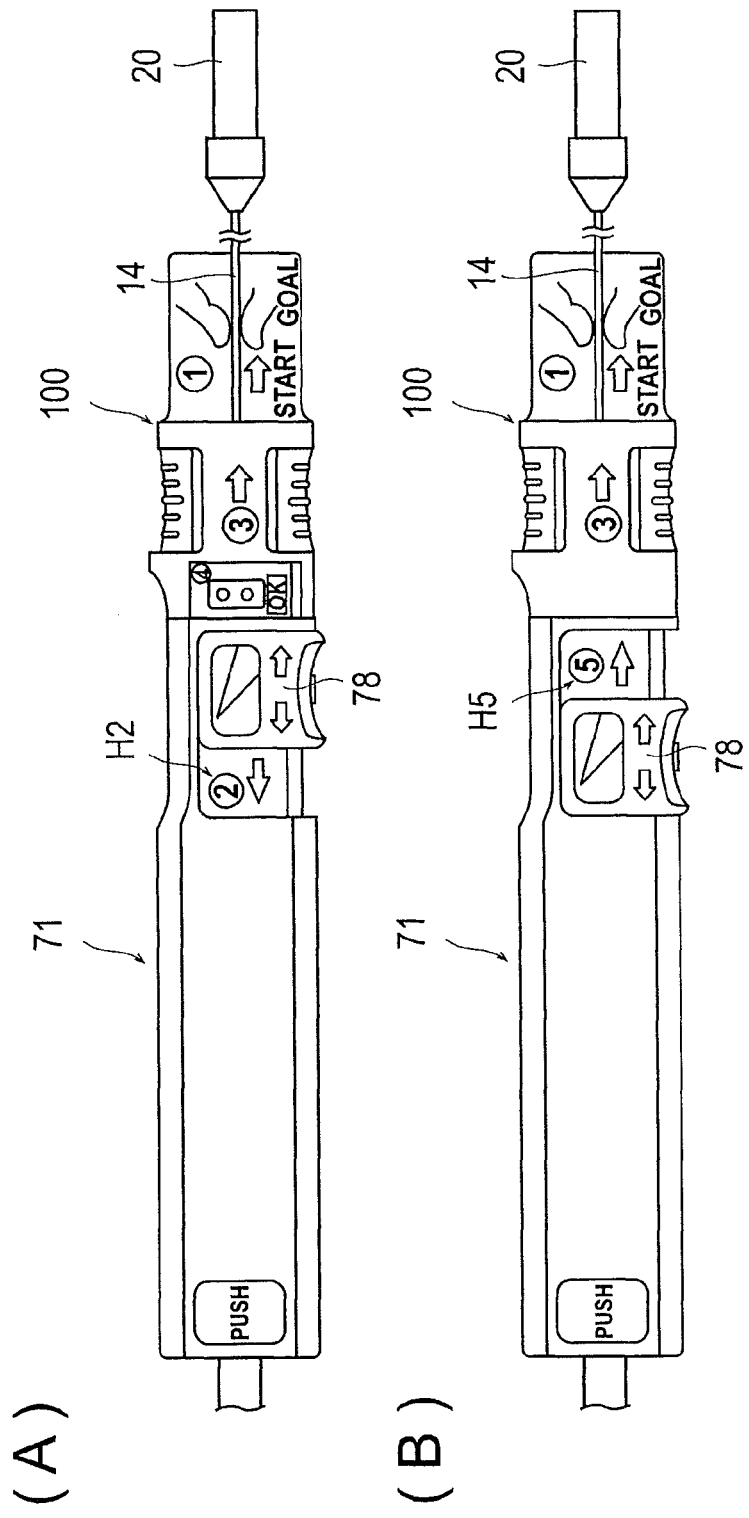

As shown in FIG. 5, the hand-side operation unit 70 is provided, in order to make processes or operations in various kinds of procedures visible, with process indicating portions H (common designation of H1 to H5) which are given various indications at the surface portion of the unit for guiding the operator so as to carry out a correct operation (see FIG. 11B for the process indicating portion H5).

The process indicating portion H includes an indicating portion H1 for a pulling process of operating the pusher piece 109 and pulling the operation wire 14; an indicating portion H2 for a sticking process in which the sticking member 12 sticks the biological tissue; an indicating portion H3 for a slide portion movement process which moves the slide portion 100 slidingly and carries out sandwiching or release of the biological tissue; an indicating portion H4 for a connection process of connecting the input connector 75 with the energy supply means 4; and an indicating portion H5 (see FIG. 11B) for a sticking unit moving-back process of moving the sticking member 12 backward from the biological tissue. As illustrated, the process indicating portion has indications for imaging respective processes by using graphic indications, numbers and arrows of movement directions respectively.

With relation to the needle operation lever 78, when moving the sticking member 12 in the sticking direction (from the state shown in FIG. 11A to the state shown in FIG. 11B), it is configured as a full-loop function such that there appears an indication of the subsequent moving direction and a number (e.g., 5) indicating the order of the operation process from the lower surface of the needle operation lever 78.

To explain the hand-side operation unit 70 in more detail, the hand-side operation unit 70 includes, as shown in FIG. 2, a main body portion 71 on the side to which the guiding catheter 3 is interlocked and a slide portion 100 which interlocks with the proximal side of the main body portion 71 through guide bars (guide units) 88A, 88B, 88C so as to approach and separate with respect to the main body portion 71, and on the upper surface of the main body portion 71, there is provided a needle operation lever 78 which operates the sticking member 12.

Figure 6:
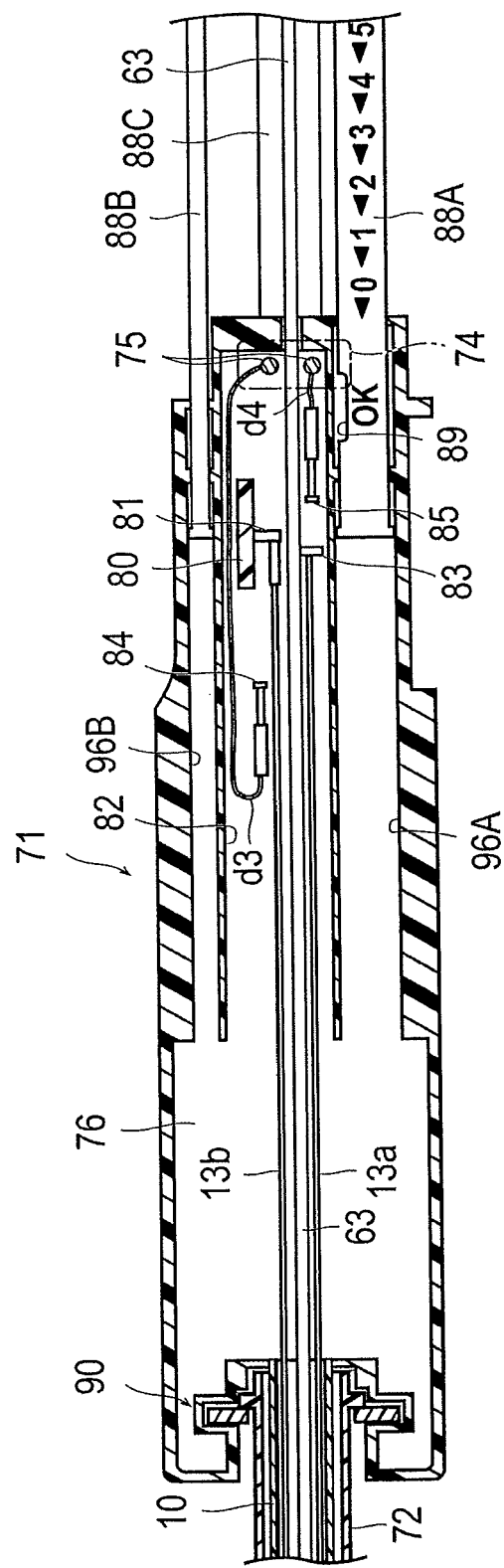
FIG. 6 is a longitudinal cross-sectional view of a portion of the hand-side operation unit shown in FIG. 2.
Figure 7:
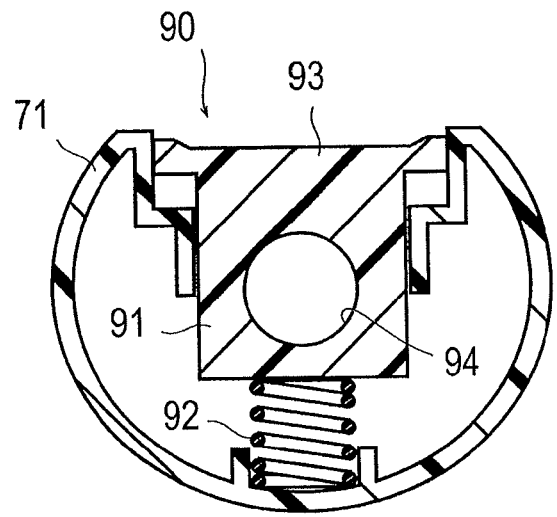
FIG. 7 is a cross-sectional view of an interlock mechanism taken along the section line 7-7 in FIG. 5.

On the surface side (upper surface side) of the main body portion 71, there is formed a concave portion 77 as shown in FIG. 5 and the needle operation lever 78 is provided slidably positioned here in the lengthwise direction (see outline arrow). As shown in FIG. 6, the needle operation lever 78 includes a bracket 80 through which a slit formed at the main body portion 71 is inserted and which protrudes so as to reach an inner space 76, and with respect to this bracket 80, there is interlocked an L-shaped terminal 81 which is provided on the proximal side of the operation member 13b for the sticking member 12. Therefore, when sliding the needle operation lever 78 along the slit, the terminal 81 slides, as shown in FIG. 5, along a guide groove 82 which is formed inside the main body portion 71 and the sticking member 12 is advanced and retracted through the operation member 13b.

The main tube 63, which is explained in more detail later, passes through the inner space 76 of the main body portion 71 approximately at the center of the inner space 76. The proximal side of the main tube 63 is interlocked with the slide portion 100 by an adhesive agent or the like (see FIG. 8), and in accordance with the slide operation of the slide portion 100, the main tube 63 slides by being guided by the main body portion 71.

A terminal 83 is attached to the main tube 63 inside the inner space 76. The terminal 83 is attached in the vicinity of the proximal end of the main tube 63 and it is configured so that also the terminal 83 slides together with the sliding of the main tube 63. That is the terminal 83 and the main tube 63 move together as a unit. To the terminal 83, the operation member 13a is connected, and the operation member 13a is arranged at a side portion of the main tube 63. At the movement termination end positions of these terminals 81, 83, there are provided contact members 84, 85 functioning as switches. The electric system of the sticking member 12 and the electric system of the sandwich member 11 are insulated so as not to be conducted.

The contact members 84, 85 are connected to both electrodes of the input connector 75 by conductive wires d3, d4, and there is employed a construction in which the contact members 84, 85 move backward while contacted by the terminals 81, 83 which move along with the movement of the operating member 13b for the sticking member 12 and the operating member 13a for the sandwich member 11. More specifically, the contact members 84, 85 and the terminals 81, 83 have contact ranges of certain lengths and so a construction is employed in which they can contact each while absorbing individual differences of the living body, whereby the contact members 84, 85 are able to move when contacted by the terminals 81, 83.

Guide bars 88A, 88B are provided in the insides of grooves 96A, 96B inside the main body portion 71, and a guide bar 88C is provided in the inside of another groove which is not shown.

The operation wire 14 is a rod provided inside the main tube 63 and which assists the operation of the clamping means K by being pulled in the axial direction, and it is configured so as to be rotatable by 360 degrees centering around the central axis inside the main tube 63. If the operation wire 14 is rotatable by 360 degrees, it is possible for the rod to pass through the foramen ovale O by inserting the distal end of the operation wire 14 as far as the vicinity of the foramen ovale O and by positionally displacing this rod in a rotational manner. According to this result, even if the state of the foramen ovale O is deformed in various ways, it is possible for the distal end of the device to pass through the foramen ovale O regardless of the shape state of the foramen ovale O, and it is possible to achieve relative easiness and speediness of the procedure.

Figure 8:
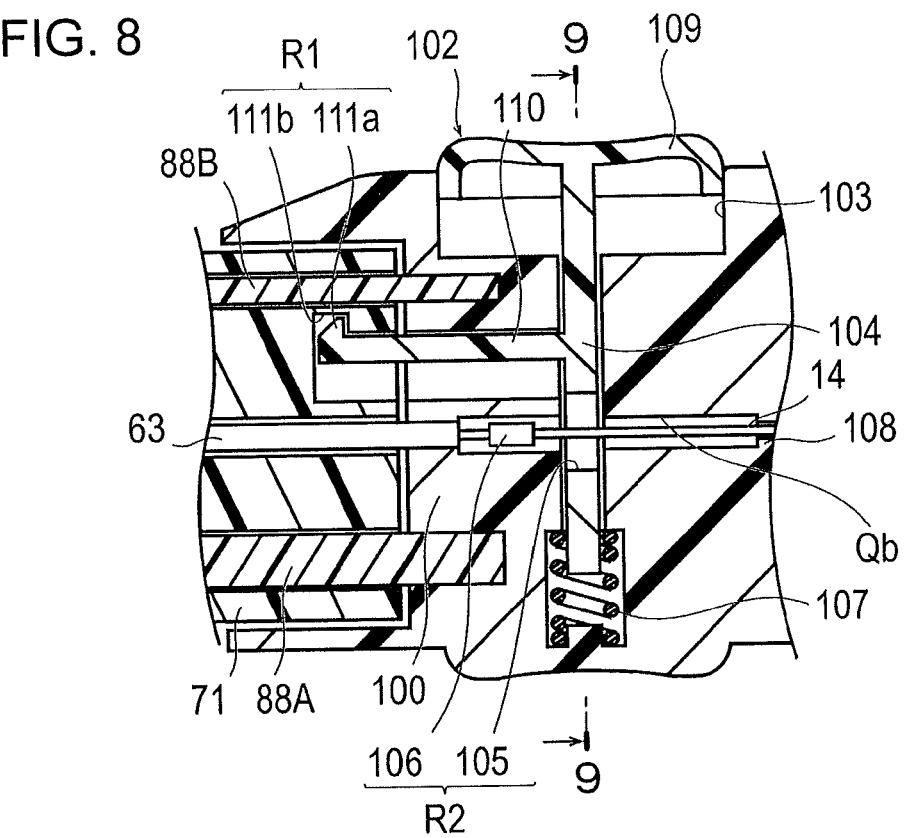
FIG. 8 is a cross-sectional view of the lock & unlock mechanism portion of the PFO closing device taken along the section line 8-8 in FIG. 5.

At the distal portion of the main body portion 71, there is provided a push button 93 of an interlock mechanism 90 (see FIG. 2). The interlock mechanism 90 is a mechanism for facilitating detachment & attachment of a Y connector 72 with respect to the main body portion 71. While pushing down the push button 93, a flange portion provided at the proximal portion of the Y connector 72 can be inserted into an insertion hole formed in the main body portion 71 as shown in FIG. 8. When the pressing force to the push button 93 is released after fitting the flange portion at the proximal portion of the Y connector 72 into the insertion hole in the main body portion 71, the flange portion of the Y connector 72 engages an engagement hole 94 of a slide member 91. The slide member 91 is acted on (biased) by a spring member 92 to exert a drop-out stopping function that inhibits or prevents the flange portion from dropping-out or being released. Pushing down the push button 93 detaches or releases the Y connector 72.

At the distal end of the hand-side operation unit 70, as shown in FIG. 2, it is preferable to interlock the Y connector 72, into which it is possible to inject a contrast agent or the like, by the interlock mechanism 90, but in a case in which the Y connector 72 is not used, a guiding catheter 3 having a flange portion can be directly interlocked with the main body portion 71.

At the proximal portion of the main body portion 71, there is provided a connection hole 74 corresponding to the exterior shape of the output connector 87 and inside this connection hole 74, there is arranged an electrode terminal of the input connector 75.

The guide bar 88A is arranged such that a portion of the lateral side of the guide bar 88A enters into the connection hole 74, and the portion of the guide bar 88A which has entered into the connection hole 74 hinders or prevents insertion of the output connector 87 into the connection hole 74 and prevents connection of the output connector 87 with the input connector 75. A portion of the lateral side of the guide bar 88A is provided with a cutout portion 89 (see FIG. 6) and when the guide bar 88A and the main tube 63 together with the slide portion 100 are moved backward with respect to the main body portion 71, the output connector 87 becomes connectable with the input connector 75 by a mechanism in which this cutout portion 89 coincides with the connection hole 74. Also, by the backward movement of the slide portion 100, the terminal 83 fixed on the main tube 63 contacts the contact member 85 and the sandwich member 11 and the input connector 75 are connected electrically.

By virtue of the construction described above, the connection between the energy supply means 4 and the input connector 75, which is the most essential procedure and for which carefulness is required, can be carried out only after the sandwiching of the biological tissue M is completed, and so the safety of the procedure is heightened.

Also, as shown in FIG. 5, the main body portion 71 is provided with a window 73 adjacent to the input connector 75. The guide bar 88A includes an "OK" indicating portion H6 in the vicinity of the cutout portion 89 and further, from the "OK" indicating portion H6, numbers (1 to 5) are sequentially set forth at a constant pitch together with triangular-shaped arrows.

When pulling-in and withdrawing the positioning hold means 60 into the inside of the catheter main body 10 by moving the slide portion 100 backward from the main body portion 71, the hand-side operation unit 70 is configured so that the numbers on the guide bar 88A appear at the window 73 sequentially so as to be counted down, and when the terminal 83 which makes the sandwich member 11 conductable contacts the contact member 85, the "OK" indicating portion H6 appears in the window 73.

Figure 9:
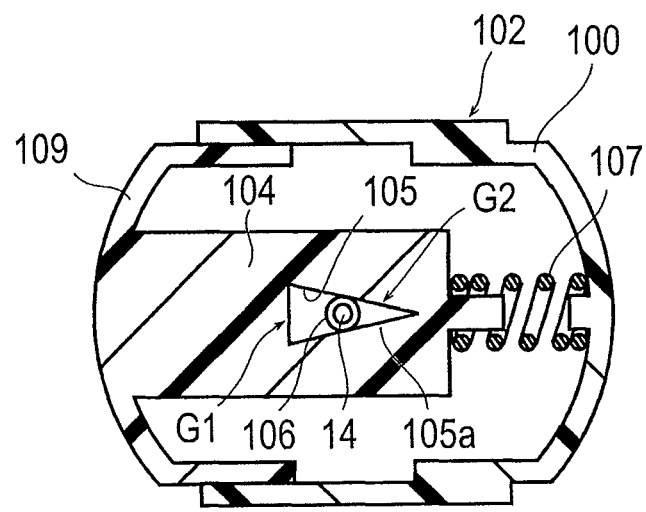
FIG. 9 is a cross-sectional view taken along the section line 9-9 in FIG. 8.

The lock & unlock mechanism 102 shown in FIGS. 8 and 9 is provided at the slide portion 100 and by pressing the pusher piece 109, the mechanism locks & unlocks the slide movement of the slide portion 100 and concurrently, locks & unlocks the axial direction movement of the operation wire 14.

The lock & unlock mechanism 102 is provided together with a first lock portion R1 for the slide portion, which interlocks the slide portion 100 and the main body portion 71 by sliding an operation member 104, makes the slide movement possible by releasing the lock and so on; and a second lock portion R2 for the operation wire, which temporarily stops the advancing and retracting operation in the axial line direction of the operation wire 14 when positioning hold means 60 described later which is provided at the distal portion of the operation wire 14 holds or positions the biological tissue M.

The first lock portion R1 includes an operation member 104 provided freely slidably inside a slide hole 103 which is formed at the slide portion 100 and a restricting rod 110 integrally formed with the operation member 104 and which restricts the movement of the slide portion 100 with respect to the main body portion 71. A spring 107 applies a biasing force to the operation member 104 and the restricting rod 110.

The restricting rod 110 is provided with a projecting engagement protrusion 111a, the distal end of which engages an engagement concave portion 111b of the main body portion 71 so that when the operation member 104 is pressed, the engagement between the engagement protrusion 111a and the engagement concave portion 111b is released and it becomes possible for the slide portion 100 to slide with respect to the main body portion 71. Therefore, if the slide portion 100 is operated backward, it is possible to operate the sandwich member 11 adjacently with respect to the sticking member 12 through the operation member 13a. In addition, the operation member 104 is provided also with the second lock portion R2 and, by pressing the operation member 104, also the second lock portion R2 is be released.

The release of the first lock portion R1 and the release of the second lock portion R2 are linked by operating the pusher piece 109 and the operation member 104 in this manner, so that it is possible to link the storing operation of the sandwich member 11 into the inside of the catheter and the operation for surely setting the operation wire 14 to be in a straight shape when pulling out the long operation wire 14 from the left atrium side, it is possible to prevent a traction operation in a state in which the operation wire 14 having a possibility of damaging the biological tissue M is curved and/or a moving-back operation of the sandwich member 11 which is in a sandwiching state, and it is possible to prevent a situation in which the biological tissue M is damaged or fractured.

The second lock portion R2 for the operation wire 14 is constituted by a locking portion 105 formed at the operation member 104 and a large diameter portion 106 which is fixed on the operation wire 14 and is larger than the outer diameter of the operation wire 14. It is possible for the material forming the large diameter portion 106 to be, for example, a stainless pipe or the like. The large diameter portion 106 is fixed with respect to the operation wire 14 in a known manner such as by welding, bonding, fusion or the like depending on the material. With respect to the second lock portion R2, in order to temporarily stop the advancing and retracting operation of the operation wire 14 in the axial direction, the locking portion 105 provided at the operation member 104 is formed as a wedge-shaped through-hole having a wide width portion G1 and a narrow width portion G2. If the wedge-shaped through-hole is employed in this manner, by only moving the operation wire 14 inside the through-hole, the sandwiching of the large diameter portion 106 becomes stronger and even if pressurizing means or the like is not provided separately, it is possible to hold the operation wire 14 to the fixing position and it is possible to carry out the procedure rather easily, safely and also reliably.

In case of carrying out a procedure, a stick or puncture operation by the sticking member 12 is carried out after the positioning hold means 60 carries out holding and/or positioning of the biological tissue M, and the holding and/or the positioning of the biological tissue M is carried out by exerting traction on the operation wire 14. Even if the holding and/or the positioning of the biological tissue M is carried out by exerting a pulling force on the operation wire 14, it is not possible to carry out the stick operation as long as the holding state and/or the positioning state are/is not maintained. Therefore, even if the second lock portion R2 engages the large diameter portion 106 with the locking portion 105 (depending on the situation, entrance edge portion 105a of a through-hole) when traction-operating the operation wire 14, the operation wire 14 is temporarily brought into a locked state and the hand grasping the operation wire 14 is released, it makes it possible to maintain the holding state and/or the positioning state and to carry out only the sticking operation by the sticking member 12 independently.

Also, if the lock is released, the distal portion of the operation wire 14 becomes straight in shape automatically by the elasticity of the elastic wires 66, 67 in the hold portion 62 and the hold state of the foramen ovale valve M2 can be released rather easily.

In the internal path through which the operation wire 14 of the slide portion 100 passes, there is formed a movement restriction-hole 108 having a size through which the large diameter portion 106 cannot pass toward the proximal direction. Therefore, when pulling the operation wire 14, the operation wire can be pulled and moved until the large diameter portion 106 fixed on the operation wire 14 reaches the movement restriction-hole 108, whereupon further operation or movement of the operation wire 14 in the proximal direction is prevented due to the large diameter portion 106 being unable to move into the movement restriction-hole 108.

The energy supply means 4 shown in FIG. 1 is means for supplying electric energy to the clamping means K and this has a known system constitution, so that a detailed explanation of the energy supply means will not be set forth. From a viewpoint of easiness of control, it is preferable to employ electrical energy supply means regardless of direct current power source or alternate current power source. However, the energy supply is not limited in this regard, and it is possible to employ any kind of means if it is possible to supply energy by which the foramen ovale valve M2 and the atrial septum secundum M1 sandwiched by the clamping means K can be fused by using heat and can be pressed and bonded by adhesive factors such as collagen, elastin and the like. For example, it is also possible to use ultrasound, laser, microwave or high frequency wave and the like.

The positioning hold means 60 includes, as shown in FIG. 2, in general, a positioning portion 61 for positioning the sticking member 12 with respect to the foramen ovale O and a hold portion 62 for holding the foramen ovale valve M2 in a non-retractable manner with respect to the sticking direction of the sticking member 12 and normally, the hold portion 62 is housed inside the guiding catheter 3, but at the time of use, it is pushed out from the guiding catheter 3 by operating the operation wire 14 and the main tube 63 as shown in the drawing.

To explain in further detail, in the center lumen L5 formed at the distal end tip 15, there are provided the main tube 63 and the operation wire 14 which is provided so as to be freely advanced and retracted in the axial direction inside the main tube 63. The main tube 63 is a tube whose proximal side is fixed at the slide portion 100 and which is positioned at or near the axial center of this device, and also, it is a tube for reinforcing the catheter main body 10 and further, it is also a tube for pulling and withdrawing the positioning hold means 60 into the catheter main body 10. The operation wire 14 passes through inside the main tube 63 from the distal end of the catheter main body 10, passes through an internal path of the slide portion 100 and protrudes from the rear end of the slide portion 100. At the proximal portion of the operation wire 14, there is interlocked the grasping unit 20 for being grasped by the operator with his fingers in order to advance and retract or to rotate the operation wire 14.

At the distal portion of the main tube 63, there is provided the positioning portion 61 of the positioning hold means 60. The positioning portion 61 is a portion for positioning the sticking member 12 with respect to the foramen ovale O and includes, as shown in FIG. 2, a pair of first elastic wires 66 which are operated expandably and contractibly by the operation of the operation wire 14. The proximal end of the first elastic wire 66 is mounted on (fixed to) the outer surface of the main tube 63 and the distal end of the first elastic wire 66 is mounted on the proximal side of the intermediate sleeve body 64 inside which the operation wire 14 passes-through.

The positioning portion 61 displaces the first elastic wires 66 outward by making the proximal end attached to the main tube 63 serve as a supporting point depending on the operation for advancing and retracting the operation wire 14 in the axial direction, depresses the inner edge of the foramen ovale O with approximately equal elastic force by the respective first elastic wires 66, and aligns the sticking member 12 with respect to the foramen ovale O. In other words, there is exerted a function in which the sticking member 12 positioned between both the first elastic wires 66 is positioned at a central portion of the foramen ovale O.

On the other hand, the hold portion 62 is a portion which holds the sticking member 12 from the rear surface side so as to stick the foramen ovale valve M2 relatively easily and includes, as shown in FIG. 2, a distal member 68 provided at the distal portion of the operation wire 14, a distal end sleeve body 65 and a pair of second elastic wires 67 by which the intermediate sleeve body 64 and the distal end sleeve body 65 are interlocked. The distal member 68 is fixed on the distal end of the operation wire 14 and with respect to the distal end sleeve body 65 and the intermediate sleeve body 64, the operation wire 14 passes-through into the inside of the distal end sleeve body 65 and the intermediate sleeve body 64. And with respect to the second elastic wire 67, the proximal end of the second elastic wire 67 is welded to the distal end of the intermediate sleeve body 64 and the distal side of the second elastic wire 67 is welded to the distal end sleeve body 65.

The second elastic wire 67 and the distal member 68 for interlocking the intermediate sleeve body 64, the distal end sleeve body 65 and both the sleeve bodies 64, 65 constitute a curving mechanism W which curves or bends the distal portion of the operation wire 14.

The curving mechanism W is a mechanism used for holding the foramen ovale valve M2. When the sticking member 12 sticks or pierces the foramen ovale valve M2, the sticking becomes easier if the thin foramen ovale valve M2 is held from the rear surface side of the foramen ovale valve M2. Therefore, the curving mechanism W is constituted such that the second elastic wire 67 is curved or bent between the distal member 68 and the distal side of the first elastic wire 66 by moving the operation wire 14 backward in the axial direction and the foramen ovale valve M2 is held from the rear surface side by the distal member 68 and the distal end sleeve body 65. In other words, the curving mechanism W is constituted such that the distal portion of the operation wire 14 is curved or bent by making the distal side of the first elastic wire 66 mounted on the main tube 63 serve as a supporting point.

However, it is necessary for the curving mechanism W of the hold portion 62 to be configured so as to be curved and hold the foramen ovale valve M2 after the first elastic wire 66 of the positioning portion 61 aligns and positions the sticking member 12 with respect to the foramen ovale O, so that it is necessary for the first elastic wire 66 to deform in advance of the second elastic wire 67, and therefore, in this embodiment disclosed by way of example, both the elastic members are made different in rigidity.

When the slide portion 100 is advanced and retracted with respect to the main body portion 71, it is possible for the main tube 63 fixed firmly to the slide portion 100 to be pulled into the inside of the lumen L5 in the center of the catheter main body 10 and along with this operation, it is possible to withdraw the whole positioning hold means 60 into the inside of the catheter main body 10.

Set forth next is a description of the operation of this embodiment

The operator inserts an introducer (dilator & long sheath) from the femoral vein. The distal end of the long sheath is made to reach the left atrium L by way of the right atrium R and thereafter, the dilator is pulled out from the long sheath.

The pusher piece 109 of the first lock portion R1 in the lock & unlock mechanism 102 is pressed in the inward direction of the slide portion 100, and the operation member 104 is lowered inside the slide hole 103 and the restriction of the restricting rod 110 is removed. Thus, the slide portion 100 shifts to a movable state with respect to the main body portion 71. A portion of the lateral side of the guide bar 88A enters into the connection hole 74, thereby hindering connection of the output connector 87 to the input connector 75, and unexpected power supply from the energy supply means 4 is suppressed reliably and safety is secured.

When the slide portion 100 is moved backward with respect to the main body portion 71 and concurrently, the needle operation lever 78 is also moved backward, there is obtained a state in which the wire member portion 11b of the sandwich member 11, the sticking member 12 and the like are stored inside the catheter main body 10.

In this state, the catheter is inserted into the inside of the long sheath and is moved to reach as far as the left atrium L passing through the femoral vein J & the right atrium R.

When the distal end of the catheter main body 10 reaches the left atrium L, the slide portion 100 progresses with respect to the main body portion 71. Thus, the flat-plate portion 11a of the sandwich member 11 protrudes from the distal end of the catheter main body 10 through the terminal and the operation member 13a, and also, the main tube 63 is moved forward and concurrently, the pusher piece 109 of the lock & unlock mechanism 102 is pressed and a state is brought about in which the large diameter portion 106 of the operation wire 14 does not abut the narrow width portion G2 of the through-hole 105 formed in the operation member 104, in other words, in which the second lock portion R2 is brought into an unlocked state and the operation wire 14 is brought into a free state.

Then, from the distal end of the main tube 63, the distal end of the operation wire 14 protrudes from the distal end sleeve body 65 and is inserted into the pulmonary vein Q. It is possible for this protrusion state to be confirmed visibly from the outside because an X-ray impermeable marker is provided on the distal member 68. The operation wire 14 is rotatable by 360 degrees, so that it can progress while rotating the operation wire 14 and it can pass rather easily through the pulmonary vein Q.

In a state in which the operation wire 14 is inserted in the pulmonary vein Q, the hand-side operation unit 70 is pulled until the sandwich member 11 reaches the right atrium R. At that time, the distal end of the operation wire 14 protrudes from the distal end sleeve body 65 and is inserted or positioned inside the left atrium L.

(1) Next will be described the traction processes of the operation wire (n the drawing, the sequence of the processes is indicated by numbers with circles, but in the description, they are indicated by numbers in parentheses. Hereinafter, a similar indication is employed.)

As shown in FIG. 5, at the indicating portion H1 of the traction process, there is applied an indication of exerting traction on the grasping unit 20 together with an indication of the number (1). In accordance with this indication, after confirming the distal end position of the operation wire 14, the operator makes, as shown in FIG. 18B, the operation wire 14 move backward by exerting traction on the grasping unit 20 until the distal member 68 at the distal end of the operation wire 14 abuts the distal end sleeve body 65 (the move-back amount is "δ1" in FIG. 18B).

When the operation wire 14 is moved backward, the large diameter portion 106 is also moved backward and in the lock & unlock mechanism 102, the operation member 104 is biased upward by the spring force of the spring 107 unless the pusher piece 109 is pressed, so that the operation wire 14 is regularly or normally compression-held between the narrow width portion G2 of the wedge-shaped through-hole 105 and the inner circumferential surface of the internal path Qb and therefore, it is possible, with respect to the moving-back of the operation wire 14, to smoothly carry out the pulling operation. Then, the main body portion 71 is operated and the second elastic wire 67, the sandwich member 11 and the sticking member 12 are positioned in the vicinity of the foramen ovale valve M2, and the whole hold portion 62 is inserted to the left atrium L side.

Figure 18:
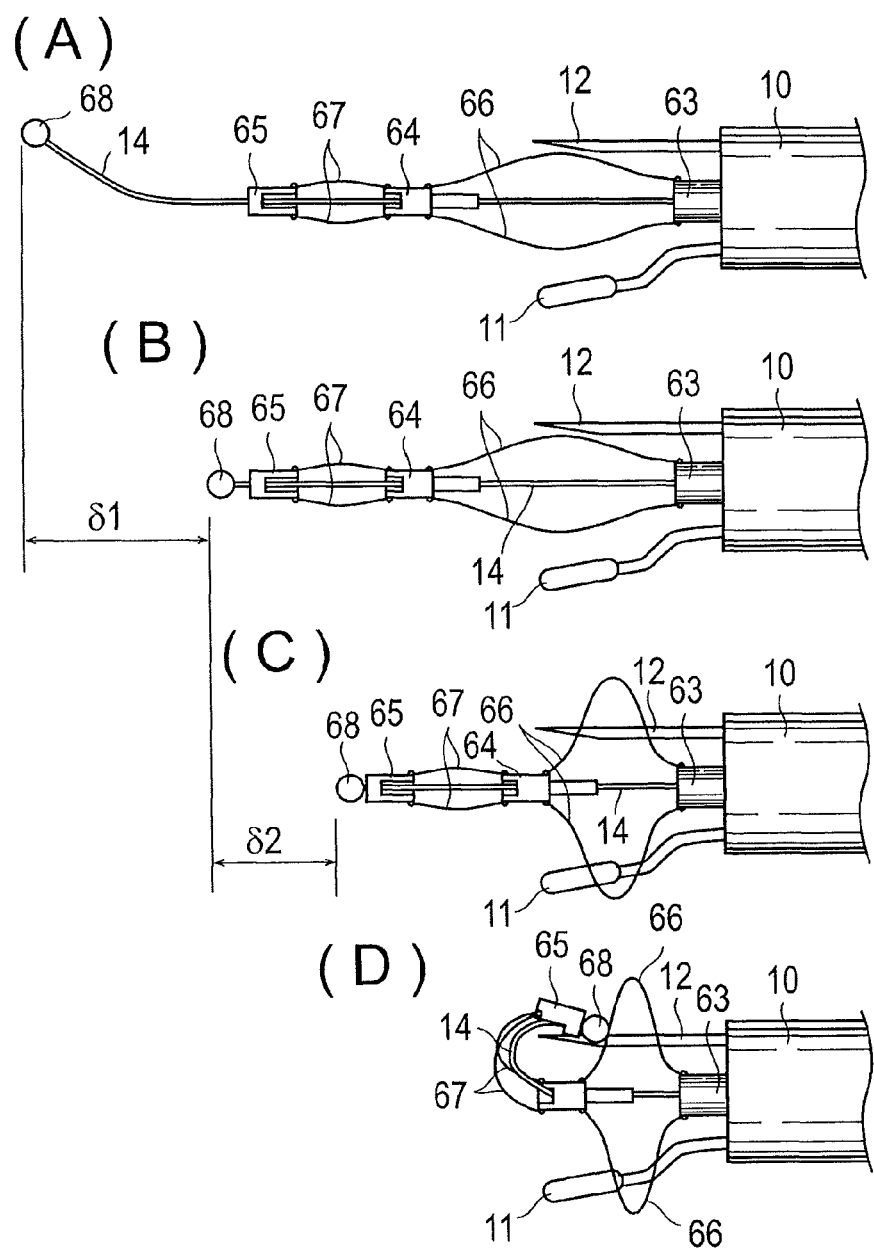
FIGS. 18A to 18D are schematic diagrams showing operation states of the PFO closing device respectively.

When the operation wire 14 is moved backward further (the moving-back amount is "δ2" in FIG. 18C), this operation force of moving backward is transmitted to the first elastic wire 66, whose proximal end is mounted on the main tube 63, through the distal member 68, the distal end sleeve body 65, the second elastic wire 67 and the intermediate sleeve body 64 by the operation wire 14, and the first elastic wire 66 is deformed in a protruding manner in an arc shape in the outward direction as shown in FIG. 18C. At this point in time, the second elastic wire 67 is not deformed.

According to this result, there occurs a situation in which the first elastic wire 66 deforms while pressing and expanding the rim portion of the foramen ovale O, so that the sticking member 12 provided just near the first elastic wire 66 is aligned with respect to the foramen ovale O and the sticking member 12 is positioned at the center of the foramen ovale O.

Figure 15:
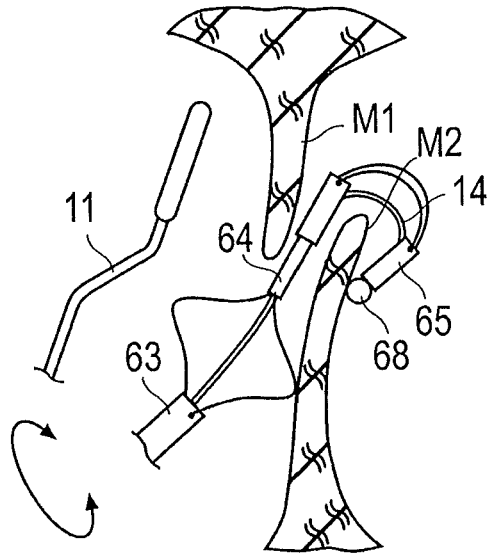
FIG. 15 is a cross-sectional schematic diagram in which an operation wire is inserted into a foramen ovale.

When the operation wire 14 is operated further so as to move backward and when the rear end of the intermediate sleeve body 64 abuts the distal end of the main tube 63 as shown in FIG. 18D, the first elastic wire 66 does not deform much and the second elastic wire 67 on the distal side deforms in a protruding manner in an arc shape toward the outward direction by the operation force. According to this result, as shown in FIG. 15, the distal member 68 and the distal end sleeve body 65 curve in the inside of the left atrium L so as to approach to the sticking member 12, so that there occurs a situation in which the distal member 68 and the distal end sleeve body 65 abut the surface on the left atrium side of the foramen ovale valve M2 and hold this.

In the second lock portion R2 for the lock & unlock mechanism 102 shown in FIGS. 8 and 9, the large diameter portion 106 is pressed into the locking portion 105 which is a wedge-shaped through-hole and the operation wire 14 is locked. According to this result, even if the operator releases a hand from the grasping unit 20, the hold state is maintained reliably and it never happens that the hold of the foramen ovale valve M2 is loosened and it is possible for the operator to progress the needle operation lever 78 with only a single hand.

Figure 10:
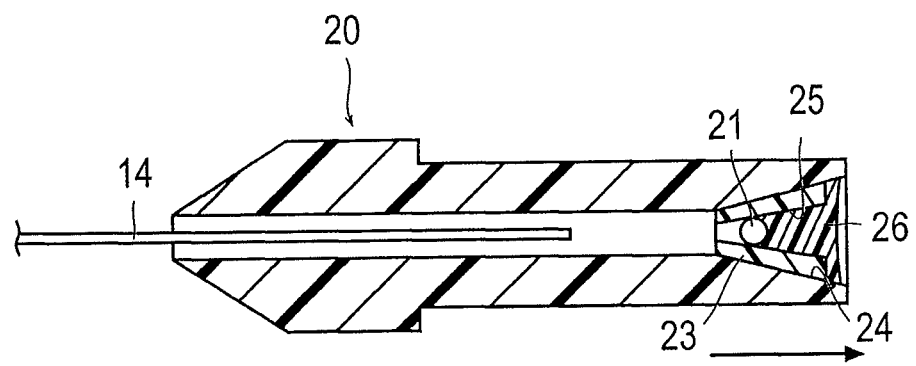
FIG. 10 is a cross-sectional view of the grasping unit when the proximal member breaks from the operation wire.

Then, in a case in which the operator pulls the grasping unit 20 too strongly in the traction process of the operation wire, the proximal member 21 breaks from the operation wire 14 as shown in FIG. 10 before the distal member 68 breaks from the operation wire 14, because the breaking strength between the operation wire 14 and the proximal member 21 is lower than the breaking strength between the operation wire 14 and the distal member 68. Consequently, a phenomenon that the distal member 68 drops out from the operation wire 14 is prevented, the distal member 68 is not left-behind inside the blood vessel, and there is prevented the possibility of causing a cerebral infarction, which is caused by a phenomenon in which the distal member 68 is carried to the brain by the blood flow. Also, even if a case should arise in which the proximal member 21 does not break from the operation wire 14, when carrying out the traction of the operation wire 14 more than necessary, the large diameter portion 106 fixed on the operation wire 14 reaches the movement restriction-hole 108 of the slide portion 100. The large diameter portion 106 cannot pass through the movement restriction-hole 108, so that the further traction of the operation wire 14 becomes impossible, and the increase of the tensile force between the operation wire 14 and the distal member 68 is restricted, thereby preventing a phenomenon in which the distal member 68 drops out from the operation wire 14. To prevent the distal member 68 from dropping out before the large diameter portion 106 reaches the movement restriction-hole 108, it is necessary to set the positional relation between the large diameter portion 106 and the movement restriction-hole 108 such that the tensile force which occurs between the operation wire 14 and the distal member 68 when the large diameter portion 106 reaches the movement restriction-hole 108 is lower than the breaking strength between the operation wire 14 and the distal member 68.

In this manner, for a safety mechanism for preventing the distal member 68 from dropping-out, this embodiment is provided with the proximal member 21 which drops out (separates from the wire 14) before the distal member 68 and the large diameter portion 106 in which the movement is restricted by the movement restriction-hole 108, and therefore, safety is improved. With regard to this safety mechanism, the proximal member 21 is not only a member which operates only in a case in which the operator pulls the grasping unit 20 too strongly but also a member which operates effectively, for example, in a case in which the distal member 68 is hooked on some object, in which an excessive force is acted between the distal member 68 and the operation wire 14.

(2) Sticking Process

Figure 16:
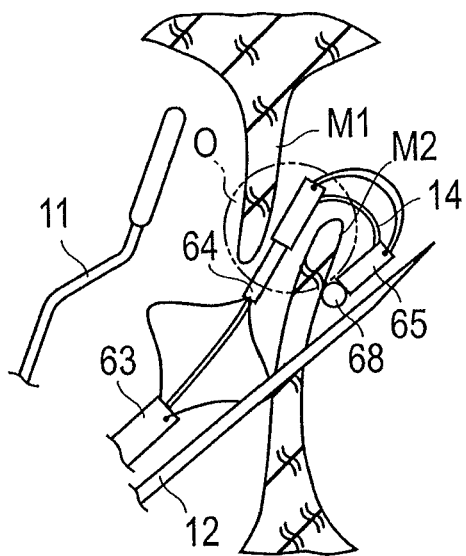
FIG. 16 is a cross-sectional schematic diagram in a state in which a foramen ovale valve is held and a sticking unit is stuck.

When the needle operation lever 78 is made to progress in the arrow direction (see FIG. 11), the sticking member 12 protrudes from the distal end of the catheter main body 10 through the operation member 13b and as shown in FIG. 16, the sticking member 12 is stuck into a predetermined position of the foramen ovale valve M2. There is no fear that there occurs a situation such as impossibility of sticking caused by looseness of the holding of the foramen ovale valve M2.

When the sticking member 12 is moved toward the sticking direction, in the hand-side operation unit 70, as shown in FIG. 11B, an indication of a next moving direction and a number indicating the sequence of the operation process appear from the bottom surface thereof.

The position of the sticking member 12 is set by the positioning hold portion 62, so that there is no fear of deviation and also, when sticking or piercing the sticking member 12 once, the position of the sticking member 12 becomes an almost fixed position in relation to the foramen ovale valve M2. Therefore, the sticking operation becomes extremely easy for the operator.

When the sticking is completed, the slide portion 100 is made to progress further with respect to the main body portion 71. Thus, the flat-plate portion 11a of the sandwich member 11 protrudes from the distal end of the catheter main body 10 through the terminal and the operation member 13a.

Then, at the hand-side operation unit 70, the terminal 81 mounted on the needle operation lever 78 progresses and contacts the contact member 84 and there is thus obtained an electrically conductive state between the sticking member 12 and the input connector 75 (see FIG. 6).

(3) Movement Process of Slide Portion

When the flat-plate portion 11a comes to a position facing the atrial septum secundum M1, the slide portion 100 is moved backward from the main body portion 71 as shown in FIG. 12A. Even at this point in time, a portion of the guide bar 88A is positioned in the connection hole 74, thereby hindering connection of the output connector 87 to the input connector 75, so that safety is secured.

Figure 17:
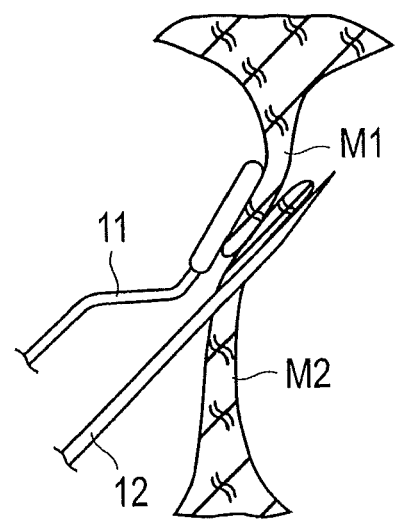
FIG. 17 is a cross-sectional schematic diagram in which a foramen ovale valve and an atrial septum secundum are sandwiched by a sticking unit and a sandwich member.

Caused by the moving-back of the slide portion 100, the flat-plate portion 11a is moved backward through the operation member 13a shown in FIG. 2, receives an influence exerted when a bend portion 11c of the wire member portion 11b enters into the inside of the lumen of the distal end tip 15, and the flat-plate portion 11a is displaced so as to approach the sticking member 12. By virtue of this displacement, the flat-plate portion 11a presses the atrial septum secundum M1 toward the foramen ovale valve M2, the positions of the atrial septum secundum M1 and the foramen ovale valve M2 in the thickness direction, in other words, the positions thereof in the forward & backward direction in the operation state, are fixed, and as shown in FIG. 17, there is obtained a state in which the atrial septum secundum M1 and the foramen ovale valve M2 exist between the sandwich member 11 and the sticking member 12.

Figure 12:
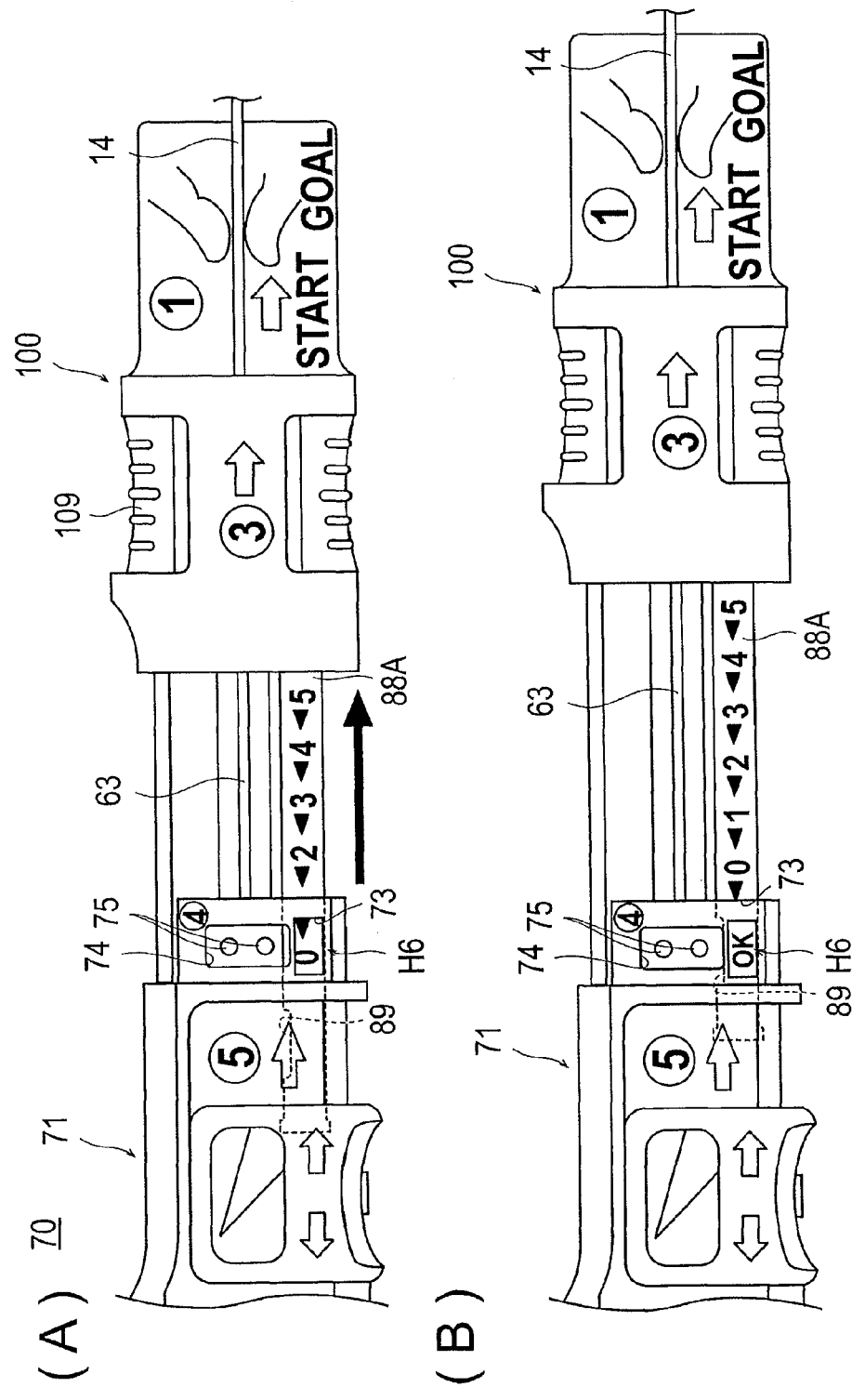

At this stage, in order to release the lock of the second lock portion R2 in the lock & unlock mechanism 102 shown in FIG. 8, 9, if the pusher piece 109 is pressed and the lock of the operation wire 14 is released, pressurization of the first elastic wire 66 and the second elastic wire 67 by the operation wire 14 and the distal member 68 disappears, and the first elastic wire 66 and the second elastic wire 67 move into a linearly extended state caused by their own elastic force. In this state, as shown in FIG. 12, when the slide portion 100 is operated so as to move backward, the whole positioning hold means 60 is withdrawn into the inside of the lumen L5 of the catheter main body 10 through the main tube 63. As shown in FIG. 12B, when the "OK" indicating portion H6 appears on the window 73, it can be understood that the withdrawal has terminated.

On the other hand, in the hand-side operation unit 70, the terminal 83 mounted on the main tube 63 also moves backward and contacts the contact member 85, and there is obtained an electrically conductive state between the sandwich member 11 and the input connector 75. Then, the cutout portion 89 of the guide bar 88A coincides with the connection hole 74 and the output connector 87 becomes connectable with the input connector 75 for the first time.

(5) Connection Process

There occurs a situation in which with respect to the moving-back of the slide portion 100 at this stage, the sandwich of the biological tissue M and the contact state of the terminal 83 and the contact member 85 are carried out all at once. Furthermore, the terminal 81 on the sticking member 12 side and the contact member 84 get into an electrically conductable state in advance, so that both of the sandwich member 11 and the sticking member 12 get into a state in which they can be supplied with electric energy.

Figure 13:
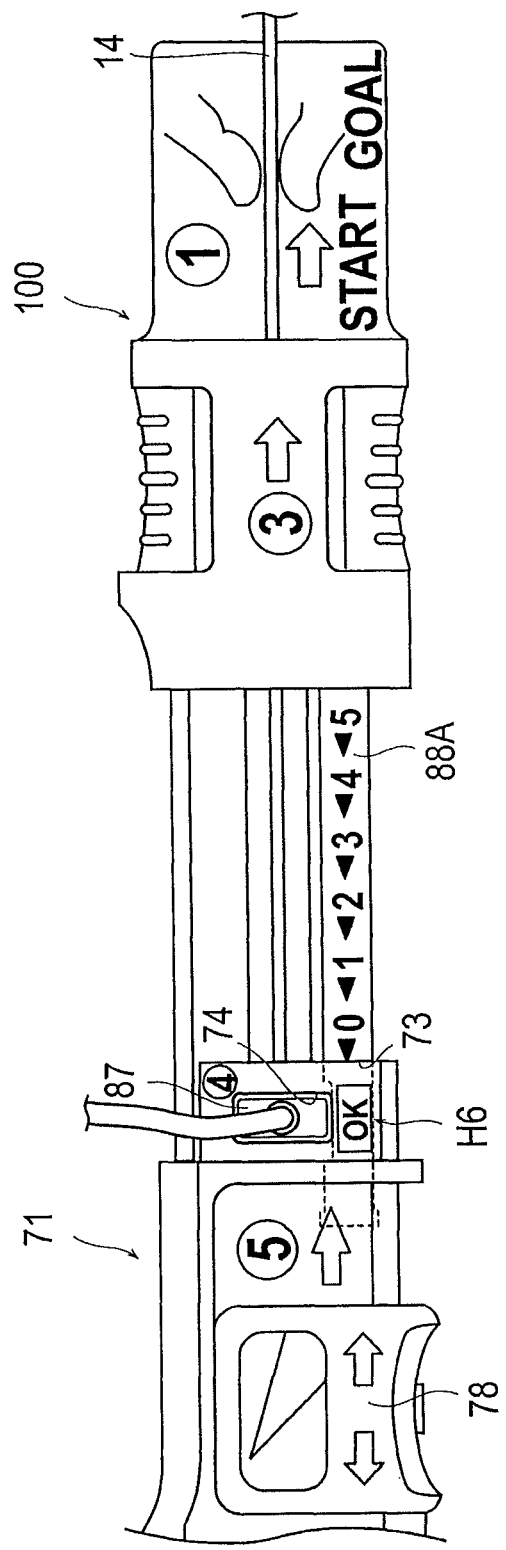
FIG. 13 is an enlarged plan view showing the hand-side operation unit when an output connector is connected to an input connector of the hand-side operation unit.

Then, as shown in FIG. 13, when the output connector 87 is connected to the input connector 75, there is obtained a state in which the power supply from the energy supply means 4 is possible.

Thereafter, by operating the switch SW, a predetermined electric energy controlled by the control unit 5 is supplied to the sandwich member 11 and the sticking member 12 through the operation members 13a, 13b and the atrial septum secundum M1 and the foramen ovale valve M2 are heated.

When the heating continues while maintaining the fusion temperature, the tissues of the atrial septum secundum M1 and the foramen ovale valve M2 melt and are fused mutually by adhesive factors such as collagen, elastin or the like. The control unit 5 of the electric energy controls the output power to be low, thereby making attachment of thrombi difficult, so that even if a portion of the sandwich member 11 and the sticking member 12 is exposed in the blood, attachment of the thrombus (thrombi) to the sandwich member 11 and the sticking member 12 can be prevented.

(6) Sticking Unit Moving-back process

Figure 14:
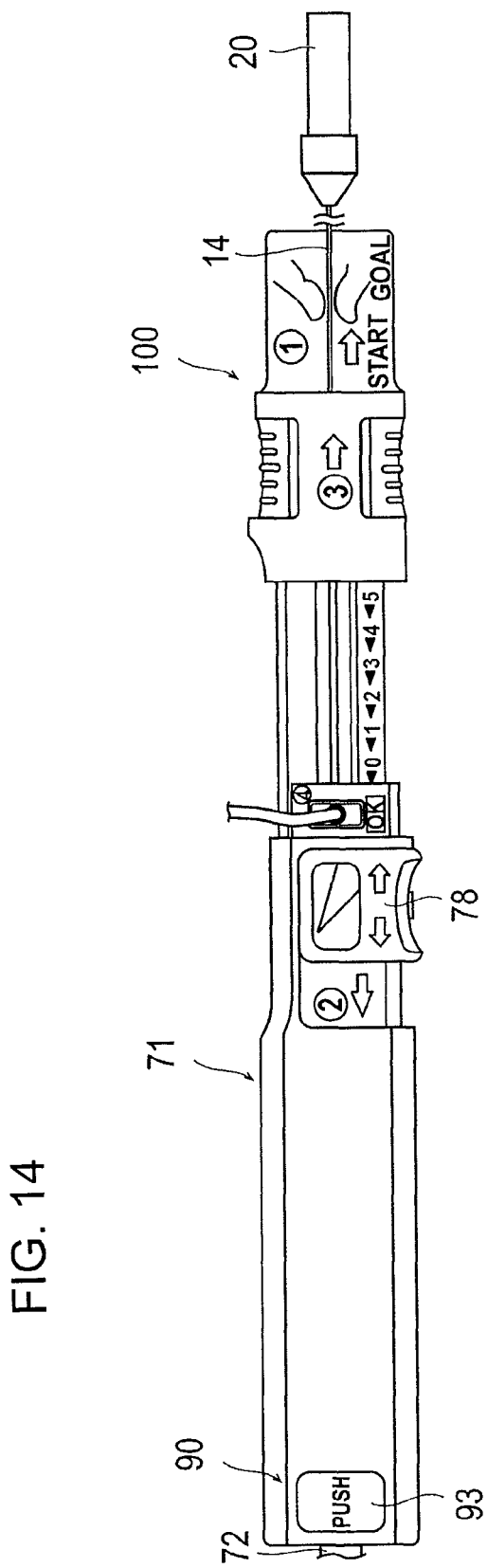
FIG. 14 is a plan view of the hand-side operation unit when a needle operation lever is moved backward.

When the fusion is completed, the needle operation lever 78 shown in FIG. 13 is moved backward in accordance with the arrow indicator indicated in the vicinity of the number (5) and is brought into the state of FIG. 14, and the sticking member 12 is housed inside the distal end tip 15. Thus, the terminal 81 which moves together with the needle operation lever 78 separates from the contact member 84 (see FIG. 6) and the electrically conductable state with respect to the clamping means K is released. Thereafter, the output connector 87 is removed from the input connector 75. Then, the push button 93 of the interlock mechanism 90 is pressed and by releasing the interlock between the Y connector 72 and the main body portion 71, the interlock between the guiding catheter 3 and the main body portion 71 is released, and when the main body portion 71 is moved backward so as to leave from the living body, the device is pulled out with the guiding catheter 3 serving as a guide. Thereafter, when the guiding catheter 3 is pulled out from the living body, the procedure is completed.

Set forth next is a description of a medical device according to a second embodiment representing another example of the medical device disclosed here. The medical device is a PFO closing device, and this second embodiment of the PFO closing device differs from the embodiment described above in terms of the construction of the grasping unit. Those portions of the PFO closing device that are the same as described above with respect to the first embodiment are identified by common reference numerals and a detailed description of such features is not repeated.

Figure 19:
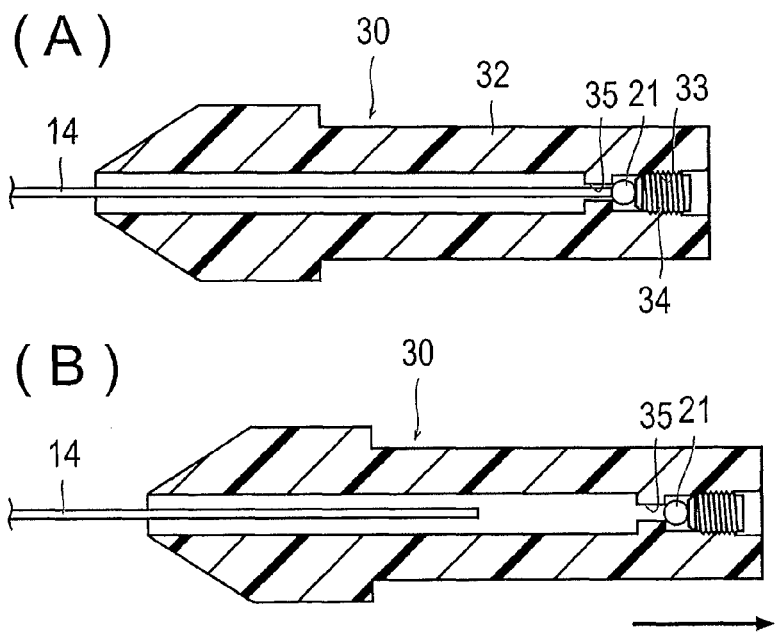

As shown in FIG. 19A, a grasping unit 30 of the PFO closing device according to the second embodiment includes a tubular grasping unit main body 32 through which the operation wire 14 passes and a screw portion 34 which is screwed into a screw groove 33 formed on the proximal side of the grasping unit main body 32. At the grasping unit main body 32, there is formed a proximal end restriction-hole 35 having a size through which the proximal member 21 cannot pass. The operation wire 14 passes through this proximal end restriction-hole 35 from the distal side of the operation wire 14, and the proximal member 21 is fixed by being pressed by the screw portion 34 on the proximal side of the proximal end restriction-hole 35. The operation wire 14 is interlocked with the grasping unit 30 only through the proximal member 21.

There is no particular limitation for the materials forming the grasping unit main body 32 and the screw portion 34, but it is possible, for example, to use the same material as that of the grasping unit main body 22 in the first embodiment discussed above.

Also in the second embodiment, similar to the first embodiment, the cross-sectional area of the interlock portion between the proximal member 21 of the operation wire 14 is configured to be smaller than the cross-sectional area of the interlock portion with respect to the distal member 68 (see FIG. 2) of the operation wire 14, and the breaking strength between the operation wire 14 and the proximal member 21 is lower than the breaking strength between the operation wire 14 and the distal member 68. Therefore, in a case in which the operator pulls the grasping unit 30 too strongly in the traction process of the operation wire in this second embodiment of the medical device, the proximal member 21 breaks from the operation wire 14 as shown in FIG. 19B before the distal member 68 breaks from the operation wire 14. Consequently, the distal member 68 is prevented from dropping out from the operation wire 14 and the distal member 68 is not to be left-behind inside the blood vessel, in which safety is improved.

Set forth next is a description of a medical device according to a third embodiment representing another example of the medical device disclosed here. The medical device is a PFO closing device, and this third embodiment of the PFO closing device differs from the embodiment described above in terms of the construction of the grasping unit and the proximal member. Those portions of the PFO closing device that are the same as described above with respect to the first embodiment are identified by common reference numerals and a detailed description of such features is not repeated.

Figure 20:
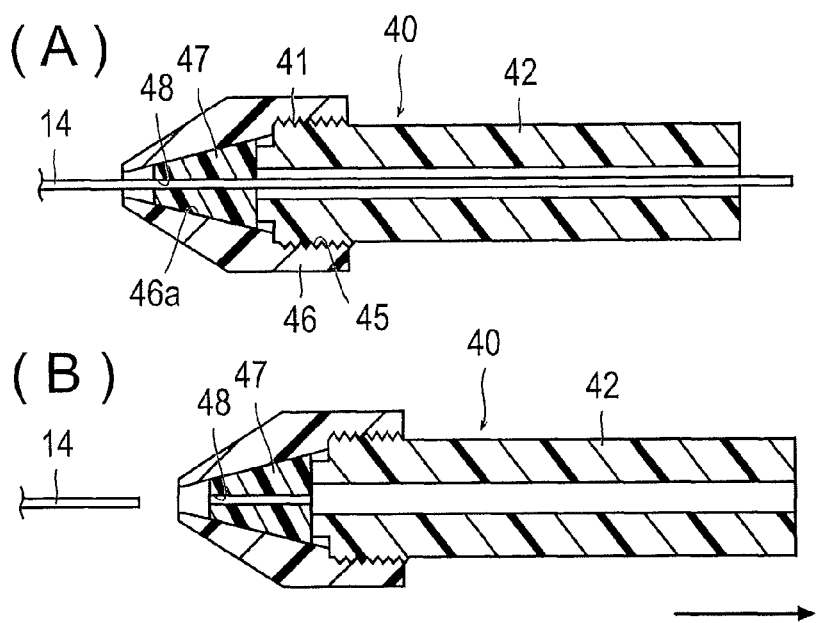

The PFO closing device according to the third embodiment is devoid of a proximal member on the proximal side of the operation wire 14 as shown in FIG. 20A. On the distal side of the operation wire 14 is fixed a distal member 68 (see FIG. 2) similar to that of the first embodiment.

The grasping unit 40 of the PFO closing device according to the third embodiment is configured so that the operation wire 14 passes through the grasping unit 40. The grasping unit 40 includes a tubular grasping unit main body 42 having a screw thread 41 formed on the outer-circumferential surface of the distal side of the tubular grasping unit main body 42, a cap 46 having a screw thread 45 that threadably engages the screw thread 41 of the grasping unit main body 42, and a wire-hold portion 47 arranged inside the cap 46 to hold the operation wire 14.

In the inside of the cap 46, there is formed a taper-shaped taper portion 46a whose inner diameter is reduced toward the distal end direction. The wire-hold portion 47 includes a taper-shaped outer-circumferential surface 47a corresponding in taper to the taper portion 46a and also is provided with a through-hole 48 having an inner diameter which is a little bit larger than the outer diameter of the operation wire 14.

When the grasping unit main body 42 is screwed into the cap 46 in a state in which the wire-hold portion 47 is arranged inside the cap 46 and the operation wire 14 passes-through into the through-hole 48 of the wire-hold portion 47, the wire-hold portion 47 is urged toward the distal end direction along the taper portion 46a and so the through-hole 48 in the wire-hold portion 47 is deformed elastically toward the diameter-reducing direction (radially inward), and the operation wire 14 is held at the wire-hold portion 47. It is possible for the wire-hold portion 47 to be formed with a slit or the like so as to be more easily deformed elastically.

Then, by adjusting the screwing amount between the cap 46 and the grasping unit main body 42, it is possible to set the holding power of the operation wire 14 to the desired amount, which depends on the wire-hold portion 47. Therefore, the holding power (hold force) can be adjusted such that the operation wire 14 will be disengaged from the wire-hold portion 47 by a load lower than the breaking strength between the operation wire 14 and the distal member 68.

The materials forming the grasping unit main body 42 and the cap 46 are not limited to specific materials, but examples of materials that can be sued are those used to fabricate the grasping unit main body 42 in the first embodiment. There is also no limitation in the particular materials for the wire-hold portion 47. Though it is preferable to us a material which is elastically deformable by screwing the grasping unit main body 42 into the cap 46. Examples of materials which can be used include a resin, elastomer or the like whose rigidity is lower than those of the grasping unit main body 42 and the cap 46.

In the medical device according to the third embodiment, the holding power of the wire-hold portion 47 with respect to the operation wire 14 is configured to be lower than the breaking strength between the operation wire 14 and the distal member 68, so that in a case in which the operator pulls the grasping unit 40 too strongly in the traction process of the operation wire, the operation wire 14 is disengaged from the wire-hold portion 47 as shown in FIG. 20A before the distal member 68 breaks from the operation wire 14. Consequently, a phenomenon that the distal member 68 drops out from the operation wire 14 is prevented and the distal member 68 is not left-behind inside the blood vessel, whereby safety is improved.

Figure 21:
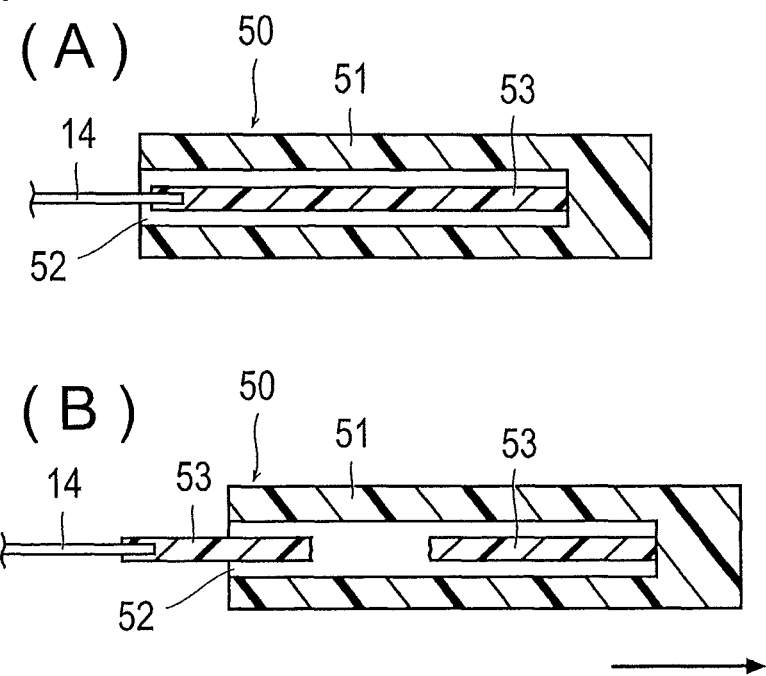

A medical device according to a fourth embodiment representing another example of the medical device disclosed here is shown in FIGS. 21A and 21B. The medical device is a PFO closing device, and this fourth embodiment of the PFO closing device differs from the embodiment described above in terms of the construction of the grasping unit and the proximal member. Other portions of the PFO closing device that are the same as described above with respect to the first embodiment are identified by common reference numerals and a detailed description of such features is not repeated.

As shown in FIG. 21A, the grasping unit 50 of this fourth embodiment of the PFO closing device includes a tubular grasping unit main body 51 having an opening portion 52 which opens toward the distal side and the operation wire 14 is interlocked to the bottom surface of the opening portion 52 through an elongated proximal member 53. On the distal side of the operation wire 14, there is fixed a distal member 68 (see FIG. 2) similar to the first embodiment.

The breaking strength of the proximal member 53 itself is configured to be lower than the breaking strength between the operation wire 14 and the distal member 68. The material forming the proximal member 53 is not particularly limited so long as the breaking strength of the proximal member 53 (i.e., the strength at which the proximal member 53 breaks when subjected to a tensile load) is lower than the breaking strength between the operation wire 14 and the distal member 68. As an example, it is preferable to use resin, elastomer or the like whose rigidity is lower than that of the operation wire 14. It is also possible to employ a configuration in which the proximal member 53 is formed by deteriorating a region on the proximal side of the operation wire 14, thus lowering the breaking strength between the proximal member 53 and the operation wire 14.

According to the medical device of the fourth embodiment, in a case in which the operator pulls the grasping unit 50 too strongly in the traction process of the operation wire, the proximal member 53 breaks as shown in FIG. 21B before the distal member 68 breaks from the operation wire 14. Consequently, a phenomenon that the distal member 68 drops out from the operation wire 14 is prevented and the distal member 68 is not left-behind inside the blood vessel, whereby safety is improved.

Figure 22:
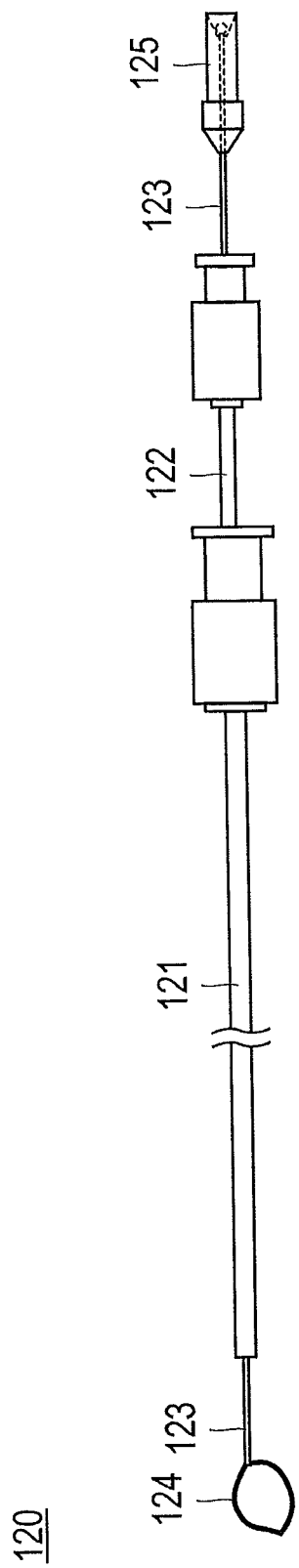
FIG. 22 is a plan view showing a snare catheter according to an embodiment disclosed by way of example.

A medical device according to a fifth exemplified embodiment is a snare catheter 120 which is used for withdrawing and removing an intravascular foreign object erroneously indwelled inside the living body, a broken piece of a catheter, a guide wire or the like, and a foreign object inside the blood vessel such as a stent or the like. As shown in FIG. 22, the snare catheter 120 includes a catheter main body 121, an introducer 122 inserted into the catheter main body 121, a snare wire 123 (operation wire) inserted into the introducer 122, a loop 124 (distal member) interlocked to the distal end of the snare wire 123 and a grasping unit 125 interlocked to the proximal end of the snare wire 123.

One of the grasping units in the first to fourth embodiments described above is applied to (is used with) the grasping unit 125 of the fifth embodiment. That is, the grasping unit shown in FIG. 22 can be any one of the grasping units described in the four embodiments described above by way of example.

When using the snare catheter 120, the loop 124 is inserted inside the blood vessel in a state of being housed in the catheter main body 121 and thereafter, the loop 124 is moved to a state in which the loop 24 protrudes from the catheter main body 121 by virtue of the grasping unit 125 and a foreign object is captured within the loop 124. Thereafter, the foreign object is pulled-in inside the catheter main body 121 by tracting the grasping unit 125 and the foreign object inside the blood vessel is withdrawn and removed. At that time, there is provided the grasping unit 125, so that when a strong tensile force acts on the snare wire 123, the snare wire 123 is disengaged from the grasping unit 125 before the loop 124 drops out from the snare wire 123 and the drop-out of the loop 124 is prevented, whereby safety is improved.

Figure 23:
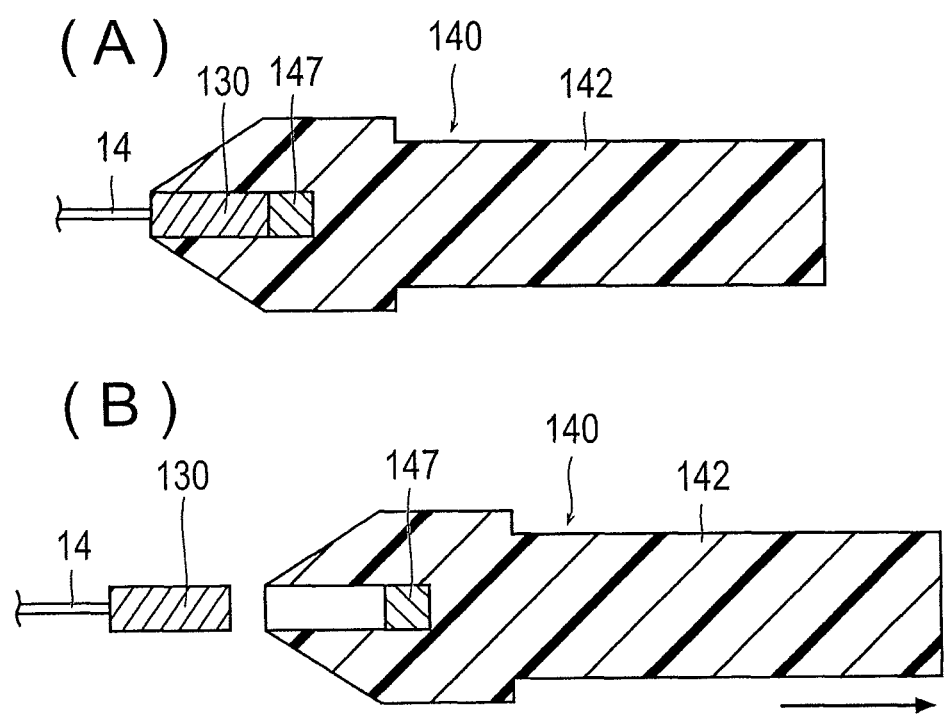

A medical device according to a sixth embodiment representing another example of the medical device disclosed here is shown in FIGS. 23A and 23B. The medical device is a PFO closing device, and this sixth embodiment of the PFO closing device differs from the embodiment described above in terms of the construction of the grasping unit and the proximal member. Other portions of the PFO closing device that are the same as described above with respect to the first embodiment are identified by common reference numerals and a detailed description of such features is not repeated.

The PFO closing device shown in FIG. 23A includes a proximal member 130 on the proximal side of the operation wire 14 and formed by a ferromagnetic body. F or the ferromagnetic body, it is possible to use iron oxide, chromium oxide, cobalt, ferrite or the like. On the distal side of the operation wire 14, there is fixed a distal member 68 (see FIG. 2) similar to that of the first embodiment.

A grasping unit 140 of the PFO closing device according to the sixth embodiment includes a tubular grasping unit main body 142 through which the operation wire 14 is passed and a wire-hold portion 147 of a ferromagnetic body, which is provided fixedly by an adhesive agent or the like in the inside of the grasping unit main body 142. The particular material; forming the grasping unit main body 142 is not limited, though it is possible, for example, to use a material similar to that of the grasping unit main body 42 in the first embodiment described above. For the ferromagnetic body, similar to the proximal member 130, it is possible to use iron oxide, chromium oxide, cobalt, ferrite or the like. The wire-hold portion 147 is interlocked with the proximal member 130 detachably by the magnetic force in the inside of the grasping unit 140. More specifically, at least one of the ferromagnetic bodies of the wire-hold portion 147 and the proximal member 130 is a magnet by virtue of being magnetized so that the wire-hold portion 147 and the proximal member 130 are coupled mutually by a magnetic force. When a tensile force having a predetermined value or more acts on the operation wire 14 (e.g., in a case in which the operator pulls the grasping unit too strongly), the coupling by the magnetic force is released and as shown in FIG. 23B, the proximal member 130 is disengaged from the wire-hold portion 147. By adjusting the materials of the ferromagnetic bodies and the sizes and shapes or the like of the proximal member 130 and the wire-hold portion 147, it is possible to set the holding power of the operation wire 14 as desired depending on the wire-hold portion 147. The holding power can thus be adjusted such that the operation wire 14 is disengaged from the wire-hold portion 147 by a load which is lower than the breaking strength between the operation wire 14 and the distal member 68.

In the medical device according to the sixth embodiment, the holding power (coupling strength by magnetic force) of the wire-hold portion 147 with respect to the operation wire 14 is configured to be lower than the breaking strength between the operation wire 14 and the distal member 68, so that in a case in which the operator pulls the grasping unit 140 too strongly in the traction process of the operation wire, as shown in FIG. 23B, the proximal member 130 and the operation wire 14 are disengaged from the wire-hold portion 147 before the distal member 68 breaks from the operation wire 14. Consequently, a phenomenon that the distal member 68 drops out from the operation wire 14 is prevented and the distal member 68 is not left-behind inside the blood vessel, whereby safety is improved. Also, the proximal member 130 and the wire-hold portion 14 are coupled by the magnetic force, so that after the proximal member 130 and the wire-hold portion 147 are separated, they can be used again by being coupled to each other.

Each of the embodiments of the medical device described above includes a safety mechanism configured so that the connection or interlock between the operation wire and the grasping unit is released by a load lower than the breaking strength between the operation wire and the distal member. That is, the medical device is configured so that an axially directed loads applied to the operation wire releases the connection between the operation wire and the grasping unit before the connection between the operation wire and the distal member is broken.

The present invention is not limited by the description above as it is possible to employ various modifications which nevertheless embody the invention here.

For example the discussion involving the first to sixth embodiments describes a device used for the treatment for closing the defect of the PFO, but the invention is not limited only to such a device, as it has useful application to close a path-shaped defect such as a left-atrial-appendage (Left Atrial Appendage) closing device or in a case in which a biological tissue M at a predetermined region is ablated. More specifically, if there is used a device which is provided, at the distal portion of the device to be passed-through inside the living body, with a distal member fixed on an operation wire which is operated on the proximal side, it is possible to apply the present invention.

The detailed description above describes a medical device in the form of a PFO closing device. But the invention here is not limited to the precise embodiments and variations described above and illustrated in the drawing figures. Various changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A medical device comprising:
at least one tubular member having a through hole, the at least one tubular member including a catheter sized and configured to be positioned in a living body, the through hole at a distal end of the tubular member possessing a size;
an operation wire positioned in the through hole and passing through the at least one tubular member so that a proximal end of the operation wire extends proximally beyond a proximal end of the at least one tubular member and a distal end of the operation wire extends distally beyond the distal end of the at least one tubular member, the operation wire being axially movable in distal and proximal directions relative to the at least one tubular member;

a distal member connected to the distal end of the operation wire at a connection, the distal member being positioned distally of the distal end of the at least one tubular member, the distal member being disconnectable from the operation wire when a load is applied to the connection which exceeds a breaking strength of the connection;

the distal member possessing a size greater than size of the through hole at the distal end of the tubular member so that the distal member is prevented from entering the through hole in the at least one tubular member when the operation member is axially moving in the proximal direction;

a grasping unit connected to the proximal end of the operation wire at a connection; and a safety mechanism operatively associated with the grasping unit and the proximal end of the operation wire which causes the grasping unit to be disconnected from the operation wire when a load less than the breaking strength is applied to the connection of the grasping unit to the operation wire;

wherein the grasping unit includes a main body possessing a tapered opening at a proximal end of the main body, a proximal end fixing member positioned in the tapered opening at a proximal end of the main body, the proximal end fixing member possessing a tapering through hole in which a distal end of the through hole is smaller in size than a proximal end of the through hole, and including a proximal member fixed to the proximal end of the operation wire, the proximal member possessing an outer dimension greater than the size of the through hole at the distal end of the through hole, and including a resin fixing the proximal end fixing member in place within the tapered opening and also fixing the proximal member in the through hole.

2. The medical device according to claim 1, wherein the grasping unit includes the main body having a proximal opening at a proximal end of the main body, a portion of the proximal opening being internally threaded, the proximal member being positioned in the proximal opening, and a proximal end restriction-hole positioned distally of the proximal opening, and an externally threaded screw member in threaded engagement with the internally threaded portion of the proximal opening, the screw member contacting the proximal member to fix the proximal member in place in the proximal opening, the proximal member possessing an outer dimension greater than a size of the proximal end restriction-hole to, prevent the proximal member from passing distally through the proximal end restriction-hole.

3. The medical device according to claim 1, wherein the grasping unit includes the main body having an externally threaded portion, and an internally threaded cap in threaded engagement with the externally threaded portion of the main body, the cap having an interior that is tapered in a narrowing manner towards a distal end of the cap, and a wire hold portion positioned in the interior of the cap at a position distal of a distal end of the main body, the wire hold portion possessing a tapered outer surface in contact with the tapered interior of the cap, the operation wire passing through an opening in the wire hold portion, and rotation of the cap relative to the main body that causes the cap to move in a proximal direction relative to the main body causing the wire hold portion to more tightly grip the operation wire.

4. The medical device according to claim 1, wherein the safety mechanism comprises the proximal member having a breaking strength less than a breaking strength between the operation wire and the distal member.

5. The medical device according to claim 1, wherein the grasping unit includes the main body provided with a wire-hold portion made of a ferromagnetic material, the proximal end of the operation wire being fixed to the proximal member made of a made of a ferromagnetic material, at least one of the wire-hold portion and the proximal member being magnetized and magnetically attracting the other of the wire-hold portion and the proximal member.

6. The medical device according to claim 1, wherein the grasping unit is connected to the operation wire by way of the proximal member fixed to the proximal end of the operation wire, the proximal member possessing a size larger than an adjoining portion of the operation wire to which the proximal member is connected.

7. The medical device according to claim 1, wherein the grasping unit includes a wire-hold portion having a through hole in which is positioned the operation wire, the wire hold portion holding the operation wire with a holding force that is adjustable.

8. A medical device comprising:

a catheter:

an operation wire passing through the catheter, the operation wire being advanceable and retractable in an axial direction with respect to the catheter, the operation wire possessing a distal end and a proximal end;

a distal member interlocked on the distal end of the operation wire;

a grasping unit interlocked on the proximal end of the operation wire; and a safety mechanism for releasing the interlock between the operation wire and the grasping unit by a load lower than a breaking strength between the operation wire and the distal member;

wherein the safety mechanism includes a proximal member fixed to the proximal end of the operation wire and concurrently interlocked with the grasping unit, the proximal member breaking with respect to the operation wire by the load lower than the breaking strength between the operation wire and the distal member; and wherein the proximal member possesses an outer diameter larger than an outer diameter of the operation wire, the grasping unit including a proximal end restriction-hole having a size through which the operation wire passes and concurrently, through which the proximal member cannot pass, and a cross-sectional area of the interlock portion with respect to the proximal member of the operation wire is smaller than a cross-sectional area of the interlock portion with respect to the distal member of the operation wire.

9. The medical device according to claim 8, wherein the breaking strength of the proximal member is lower than the breaking strength between the operation wire and the distal member.

10. The medical device according to claim 8, wherein the safety mechanism is provided at the grasping unit and includes a wire-hold portion through which the operation wire passes, the wire-hold portion holding the operation wire by a holding power in which the operation wire is released by the wire-hold portion by a load lower than the breaking strength between the operation wire and the distal member.

11. The medical device according to claim 8, wherein a large diameter portion larger than an outer diameter of the operation wire is fixed to the operation wire, and a movement restriction-hole at the proximal end of the catheter, the movement restriction-hole possessing a size through which the operation wire passes and concurrently, through which the large diameter portion cannot pass toward a proximal end direction.

12. The medical device according to claim 8, wherein the grasping unit includes a main body possessing a tapered opening at a proximal end of the main body, a proximal end fixing member positioned in the tapered opening at a proximal end of the main body, the proximal end fixing member possessing a tapering through hole in which a distal end of the through hole is smaller in size than a proximal end of the through hole, the proximal member possessing an outer dimension greater than the size of the through opening at the distal end of the through hole, and including a resin fixing the proximal end fixing member in place within the tapered opening and also fixing the proximal member in the through opening.

13. The medical device according to claim 8, wherein the grasping unit includes a main body having a proximal opening at a proximal end of the main body, a portion of the proximal opening being internally threaded, the proximal member being positioned in the proximal opening, and a proximal end restriction-hole positioned distally of the proximal opening, and an externally threaded screw member in threaded engagement with the internally threaded portion of the proximal opening, the screw member contacting the proximal member to fix the proximal member in place in the proximal opening, the proximal member possessing an outer dimension greater than a size of the proximal end restriction-hole to, prevent the proximal member from passing distally through the proximal end restriction-hole.

14. The medical device according to claim 8, wherein the grasping unit includes a main body having an externally threaded portion, and an internally threaded cap in threaded engagement with the externally threaded portion of the main body, the cap having an interior that is tapered in a narrowing manner towards a distal end of the cap, and a wire hold portion positioned in the interior of the cap at a position distal of a distal end of the main body, the wire hold portion possessing a tapered outer surface in contact with the tapered interior of the cap, the operation wire passing through an opening in the wire hold portion, and rotation of the cap relative to the main body that causes the cap to move in a proximal direction relative to the main body causing the wire hold portion to more tightly grip the operation wire.

15. The medical device according to claim 8, wherein the grasping unit includes a main body fixed to the operation wire by way of the proximal member, the safety mechanism comprising the proximal member having a breaking strength less than a breaking strength between the operation wire and the distal member.

16. The medical device according to claim 8, wherein the grasping unit includes a main body provided with a wire-hold portion made of a ferromagnetic material, the proximal end of the operation wire being fixed to the proximal member made of a ferromagnetic material, at least one of the wire-hold portion and the proximal member being magnetized and magnetically attracting the other of the wire-hold portion and the proximal member.

17. A medical device comprising:
a catheter;
an operation wire passing through the catheter, the operation wire being advanceable and retractable in an axial direction with respect to the catheter, the operation wire possessing a distal end and a proximal end;
a distal member interlocked on the distal end of the operation wire;
a grasping unit interlocked on the proximal end of the operation wire; and
a safety mechanism for releasing the interlock between the operation wire and the grasping unit by a load lower than a breaking strength between the operation wire and the distal member;
wherein a large diameter portion larger than an outer diameter of the operation wire is fixed to the operation wire, and a movement restriction-hole at the proximal end of the catheter, the movement restriction-hole possessing a size through which the operation wire passes and concurrently, through which the large diameter portion cannot pass toward a proximal end direction.

\* \* \* \* \*